United States Patent
Ratner et al.

(10) Patent No.: US 9,599,613 B2
(45) Date of Patent: Mar. 21, 2017

(54) PHOTONIC BLOOD TYPING

(75) Inventors: Daniel M. Ratner, Seattle, WA (US); Jill M. Johnsen, Seattle, WA (US); James T. Kirk, Seattle, WA (US); José A. López, Seattle, WA (US); Norman D. Brault, Seattle, WA (US); Shaoyi Jiang, Redmond, WA (US)

(73) Assignees: University of Washington through its Center for Commercialization, Seattle, WA (US); Puget Sound Blood Center, Seattle, WA (US)

( * ) Notice: Subject to any disclaimer, the term of this patent is extended or adjusted under 35 U.S.C. 154(b) by 0 days.

(21) Appl. No.: 14/234,134

(22) PCT Filed: Jul. 20, 2012

(86) PCT No.: PCT/US2012/047745
§ 371 (c)(1),
(2), (4) Date: May 23, 2014

(87) PCT Pub. No.: WO2013/013220
PCT Pub. Date: Jan. 24, 2013

(65) Prior Publication Data
US 2014/0315760 A1    Oct. 23, 2014

Related U.S. Application Data

(60) Provisional application No. 61/509,776, filed on Jul. 20, 2011, provisional application No. 61/588,785, filed on Jan. 20, 2012.

(51) Int. Cl.
G01N 33/80    (2006.01)
G01N 33/543   (2006.01)
G01N 21/75    (2006.01)

(52) U.S. Cl.
CPC ....... *G01N 33/54373* (2013.01); *G01N 33/80* (2013.01); *G01N 21/75* (2013.01)

(58) Field of Classification Search
CPC .................................................... G01N 33/80
See application file for complete search history.

(56) References Cited

U.S. PATENT DOCUMENTS 3,671,502 A    6/1972  Samour
4,075,183 A    2/1978  Kawakami
(Continued)

FOREIGN PATENT DOCUMENTS

DE    10 2006 004 111 A1    8/2007
EP        0 354 984 A2        2/1990
(Continued)

OTHER PUBLICATIONS

Vaisocherova et al., Ultralow Fouling and Functionalizable Surface Chemistry Based on a Zwitterionic Polymer Enabling Sensitive and Specific Protein Detection in Undiluted Blood Plasma, Analytical Chemistry, vol. 80, No. 20, Published online Sep. 23, 2008, pp. 7894-7901.*

(Continued)

*Primary Examiner* — Rebecca Martinez
(74) *Attorney, Agent, or Firm* — Chirstensen O'Connor Johnson Kindness PLLC

(57) ABSTRACT

Photonic devices, systems, and methods for detecting an analyte in a biological solution (e.g., whole blood) are provided. Representative photonic devices are optical ring resonators having nanoscale features and micron-sized diameters. Due to the compact size of these devices, many resonators can be disposed on a single substrate and tested simultaneously as a sample is passed over the devices. Typical analytes include blood cells, antibodies, and pathogens, as well as compounds indicative of the presence of (Continued)

blood cells or pathogens (e.g., serology). In certain embodiments, blood type can be determined through photonic sensing using a combination of direct detection of blood cells and serology. By combining the detection signals of multiple devices, the type of blood can be determined.

22 Claims, 21 Drawing Sheets

(56) References Cited

U.S. PATENT DOCUMENTS

| | | | |
|---|---|---|---|
| 4,138,446 A | 2/1979 | Kawakami |
| 4,415,388 A | 11/1983 | Korpman |
| 4,493,926 A | 1/1985 | Williams, Jr. |
| 4,985,023 A | 1/1991 | Blank |
| 5,204,060 A | 4/1993 | Allenmark |
| 5,233,453 A | 8/1993 | Sivarajan |
| 5,633,724 A | 5/1997 | King |
| 5,638,396 A | 6/1997 | Klimek |
| 5,714,360 A | 2/1998 | Swan |
| 5,776,711 A | 7/1998 | Vyas et al. |
| 5,781,284 A | 7/1998 | Infante |
| 5,804,453 A | 9/1998 | Chen |
| 5,838,870 A | 11/1998 | Soref |
| 5,919,523 A | 7/1999 | Sundberg |
| 5,952,035 A | 9/1999 | Erb et al. |
| 5,986,042 A | 11/1999 | Irizato |
| 6,330,388 B1 | 12/2001 | Bendett |
| 6,361,768 B1 | 3/2002 | Galleguillos |
| 6,370,406 B1 | 4/2002 | Wach |
| 6,486,333 B1 | 11/2002 | Murayama |
| 6,488,896 B2 | 12/2002 | Weigl |
| 6,558,626 B1 | 5/2003 | Aker |
| 6,570,893 B1 | 5/2003 | Libatique |
| 6,661,950 B1 | 12/2003 | Strecker |
| 6,781,696 B1 | 8/2004 | Rosenberger |
| 6,782,205 B2 | 8/2004 | Trisnadi |
| 6,831,938 B1 | 12/2004 | Gunn, III |
| 6,834,152 B2 | 12/2004 | Gunn, III |
| 6,839,488 B2 | 1/2005 | Gunn, III |
| 6,853,756 B2 | 2/2005 | Gerlach |
| 6,888,973 B2 | 5/2005 | Kolodziejski |
| 6,897,263 B2 | 5/2005 | Hell |
| 6,917,727 B2 | 7/2005 | Gunn, III |
| 6,920,272 B2 | 7/2005 | Wang |
| 7,008,559 B2 | 3/2006 | Chen |
| 7,027,476 B2 | 4/2006 | Taghavi-Larigani |
| 7,056,532 B1 | 6/2006 | Kabanov |
| 7,067,072 B2 | 6/2006 | Chen |
| 7,067,342 B2 | 6/2006 | Zia |
| 7,075,954 B2 | 7/2006 | Ledentsov |
| 7,082,235 B2 | 7/2006 | Gunn, III |
| 7,095,010 B2 | 8/2006 | Scherer |
| 7,120,338 B2 | 10/2006 | Gunn, III |
| 7,126,136 B2 | 10/2006 | Chen |
| 7,127,147 B2 | 10/2006 | Gunn, III |
| 7,139,459 B2 | 11/2006 | Kochergin |
| 7,145,165 B2 | 12/2006 | Cox |
| 7,164,821 B2 | 1/2007 | Gunn, III |
| 7,167,606 B2 | 1/2007 | Gunn, III |
| 7,167,615 B1 | 1/2007 | Wawro |
| 7,177,492 B2 | 2/2007 | Strecker |
| 7,212,701 B2 | 5/2007 | Strecker |
| 7,228,016 B2 | 6/2007 | Beausoleil |
| 7,244,926 B2 | 7/2007 | Ja |
| 7,266,271 B2 | 9/2007 | Strecker |
| 7,291,427 B2 | 11/2007 | Kawamura |
| 7,306,625 B1 | 12/2007 | Stratford |
| 7,307,719 B2 | 12/2007 | Wang |
| 7,309,628 B2 | 12/2007 | Zia |
| 7,315,679 B2 | 1/2008 | Hochberg |
| 7,324,199 B2 | 1/2008 | Ja |
| 7,335,248 B2 | 2/2008 | Abou-Nemeh |
| 7,336,859 B2 | 2/2008 | Sanders |
| 7,361,501 B2 | 4/2008 | Koo |
| 7,368,281 B2 | 5/2008 | Mozdy |
| 7,397,043 B2 | 7/2008 | Ja |
| 7,400,399 B2 | 7/2008 | Wawro |
| 7,419,636 B2 | 9/2008 | Aker |
| 7,419,638 B2 | 9/2008 | Saltsman |
| 7,435,944 B2 | 10/2008 | Ja |
| 7,462,325 B2 | 12/2008 | Hancock |
| 7,488,930 B2 | 2/2009 | Ajgaonkar |
| 7,497,992 B2 | 3/2009 | Cunningham |
| 7,501,092 B2 | 3/2009 | Chen |
| 7,508,849 B2 | 3/2009 | Tanaka |
| 7,519,257 B2 | 4/2009 | Lipson |
| 7,528,403 B1 | 5/2009 | Borselli |
| 7,538,329 B2 | 5/2009 | Chen |
| 7,539,369 B2 | 5/2009 | Yamazaki |
| 7,544,506 B2 | 6/2009 | Breidford |
| 7,616,850 B1 | 11/2009 | Watts |
| 7,634,165 B2 | 12/2009 | Wang |
| 7,639,723 B2 | 12/2009 | Yamazaki |
| 7,643,710 B1 | 1/2010 | Liu |
| 7,648,835 B2 | 1/2010 | Breidford |
| 7,664,157 B2 | 2/2010 | Yamazaki |
| 7,693,369 B2 | 4/2010 | Fan |
| 7,713,689 B2 | 5/2010 | Chilkoti |
| 7,737,224 B2 | 6/2010 | Willis |
| 7,738,527 B2 | 6/2010 | He |
| 7,763,453 B2 | 7/2010 | Clemmens |
| 7,773,642 B2 | 8/2010 | Yamazaki |
| 7,778,499 B2 | 8/2010 | Janz |
| 7,783,144 B2 | 8/2010 | Chigrinov |
| RE41,643 E | 9/2010 | Garbuzov |
| 7,796,262 B1 | 9/2010 | Wang |
| 7,799,573 B2 | 9/2010 | Deans |
| 7,825,380 B2 | 11/2010 | Puscasu |
| 7,826,688 B1 | 11/2010 | Sadagopan |
| 7,831,123 B2 | 11/2010 | Sparacin |
| 7,831,298 B1 | 11/2010 | Wang |
| 7,835,006 B2 | 11/2010 | Ja |
| 7,853,108 B2 | 12/2010 | Popovic |
| 7,879,444 B2 | 2/2011 | Jiang |
| 7,903,909 B2 | 3/2011 | Popovic |
| 7,936,463 B2 | 5/2011 | Kiesel |
| 7,955,836 B2 | 6/2011 | Clemmens |
| 7,961,988 B2 | 6/2011 | Krug |
| 7,968,848 B2 | 6/2011 | Johnson |
| 7,970,244 B2 | 6/2011 | Krug |
| 7,973,696 B2 | 7/2011 | Puscasu |
| 7,982,878 B1 | 7/2011 | Ja |
| 7,983,517 B1 | 7/2011 | Watts |
| 7,999,938 B2 | 8/2011 | Wang |
| 8,000,565 B2 | 8/2011 | Liu |
| 8,019,185 B2 | 9/2011 | Yap |
| 8,045,834 B2 | 10/2011 | Painter |
| 8,064,490 B2 | 11/2011 | Okayama |
| 8,068,706 B2 | 11/2011 | Popovic |
| 8,076,090 B2 | 12/2011 | Fang |
| 8,094,987 B2 | 1/2012 | Martin Armani |
| 8,111,401 B2 | 2/2012 | Magnusson |
| 8,111,402 B2 | 2/2012 | Le |
| 8,116,603 B2 | 2/2012 | Popovic |
| 8,120,782 B2 | 2/2012 | Kiesel |
| 8,139,904 B2 | 3/2012 | Green |
| 8,195,011 B2 | 6/2012 | Goldring |
| 8,195,014 B2 | 6/2012 | Heideman |
| 8,213,751 B1 | 7/2012 | Ho |
| 8,244,077 B1 | 8/2012 | Yap |
| 8,263,986 B2 | 9/2012 | Hajj-Hassan |
| 8,270,789 B2 | 9/2012 | Ogawa |
| 8,270,790 B2 | 9/2012 | Ogawa |
| 8,288,157 B2 | 10/2012 | Duer |
| 8,295,315 B2 | 10/2012 | Ward |
| 8,307,724 B1 | 11/2012 | Wichert |
| 8,447,145 B2 | 5/2013 | Goldring |
| 8,467,858 B2 | 6/2013 | Vertikov |
| 8,493,560 B2 | 7/2013 | Shopova |
| 8,835,144 B2 | 9/2014 | Jiang et al. |
| 2002/0127236 A1* | 9/2002 | Rodkey ............... C07K 14/705 |
| | | 424/185.1 |

(56) References Cited

U.S. PATENT DOCUMENTS

| | | |
|---|---|---|
| 2002/0128234 A1 | 9/2002 | Hubbell |
| 2003/0059853 A1 | 3/2003 | Lockhart |
| 2003/0143580 A1 | 7/2003 | Straus |
| 2004/0063881 A1 | 4/2004 | Lewis |
| 2004/0121337 A1 | 6/2004 | Deans |
| 2005/0054908 A1 | 3/2005 | Blank |
| 2005/0058689 A1 | 3/2005 | McDaniel |
| 2006/0116562 A1 | 6/2006 | Acosta |
| 2006/0140240 A1 | 6/2006 | Chen |
| 2006/0183863 A1 | 8/2006 | Huang |
| 2006/0193550 A1 | 8/2006 | Wawro |
| 2006/0194008 A1 | 8/2006 | Schwartz |
| 2006/0196253 A1 | 9/2006 | Crawley |
| 2006/0240072 A1 | 10/2006 | Chudzik |
| 2006/0255292 A1 | 11/2006 | Ja |
| 2006/0270064 A1 | 11/2006 | Gordon |
| 2007/0036479 A1* | 2/2007 | Beausoleil ............ 385/12 |
| 2007/0042198 A1 | 2/2007 | Schonemyr |
| 2007/0104654 A1 | 5/2007 | Hsieh |
| 2007/0111321 A1 | 5/2007 | Deans |
| 2007/0133001 A1 | 6/2007 | Cox |
| 2007/0224652 A1 | 9/2007 | Holgersson |
| 2008/0131393 A1 | 6/2008 | Yeung |
| 2008/0131939 A1 | 6/2008 | Roper |
| 2008/0160600 A1 | 7/2008 | Zuccato |
| 2008/0181861 A1 | 7/2008 | Jiang |
| 2008/0193076 A1 | 8/2008 | Witzens |
| 2008/0248578 A1 | 10/2008 | Deans |
| 2008/0299177 A1 | 12/2008 | Hardy |
| 2008/0316485 A1 | 12/2008 | Wawro |
| 2009/0017455 A1 | 1/2009 | Kwong |
| 2009/0068668 A1 | 3/2009 | Duer |
| 2009/0068726 A1 | 3/2009 | Magnin |
| 2009/0156460 A1 | 6/2009 | Jiang |
| 2009/0197791 A1 | 8/2009 | Balastre |
| 2009/0259015 A1 | 10/2009 | Jiang |
| 2009/0325211 A1 | 12/2009 | Fang |
| 2010/0099160 A1 | 4/2010 | Jiang |
| 2010/0247614 A1 | 9/2010 | Jiang |
| 2010/0248391 A1 | 9/2010 | Garcia Tello |
| 2010/0249267 A1 | 9/2010 | Jiang |
| 2011/0039717 A1 | 2/2011 | Kwong |
| 2011/0039730 A1 | 2/2011 | Erickson |
| 2011/0045472 A1 | 2/2011 | Gunn, III |
| 2011/0097277 A1 | 4/2011 | Jiang |
| 2011/0105712 A1 | 5/2011 | Jiang |
| 2011/0116093 A1 | 5/2011 | Liu |
| 2011/0129846 A1 | 6/2011 | Huh |
| 2011/0133063 A1 | 6/2011 | Ji |
| 2011/0142396 A1 | 6/2011 | Okamoto |
| 2011/0158582 A1 | 6/2011 | Su |
| 2011/0195104 A1 | 8/2011 | Jiang |
| 2011/0282005 A1 | 11/2011 | Jiang |
| 2012/0069331 A1 | 3/2012 | Shopova |
| 2012/0092650 A1 | 4/2012 | Gunn, III |
| 2012/0107946 A1 | 5/2012 | Deans |
| 2012/0195332 A1 | 8/2012 | Yoffe |
| 2012/0225474 A1 | 9/2012 | Wagner |
| 2012/0225475 A1 | 9/2012 | Wagner |
| 2012/0258549 A1 | 10/2012 | Lu |
| 2012/0276549 A1 | 11/2012 | Cunningham |
| 2013/0071061 A1 | 3/2013 | Tu |
| 2013/0083815 A1 | 4/2013 | Fang |
| 2013/0109941 A1 | 5/2013 | Li |
| 2013/0144148 A1 | 6/2013 | Li |
| 2014/0315760 A1 | 10/2014 | Ratner |
| 2014/0370567 A1 | 12/2014 | Jiang et al. |

FOREIGN PATENT DOCUMENTS

| | | |
|---|---|---|
| EP | 0 419 654 A1 | 4/1991 |
| EP | 0 479 245 A2 | 4/1992 |
| EP | 1263533 B1 | 3/2010 |
| EP | 1773481 B1 | 8/2010 |
| EP | 2229583 A2 | 9/2010 |
| EP | 2347247 A2 | 7/2011 |
| JP | 63-234007 A | 9/1988 |
| JP | 3-110473 A | 5/1991 |
| JP | 10-132732 A | 5/1998 |
| JP | 2007-130194 A | 5/2007 |
| JP | 4733331 B2 | 7/2011 |
| JP | 4758891 B2 | 2/2012 |
| JP | 4885852 B2 | 2/2012 |
| SU | 1780673 A1 | 12/1992 |
| WO | 98/16831 A1 | 4/1998 |
| WO | 00/39176 A1 | 7/2000 |
| WO | 03/023474 A1 | 3/2003 |
| WO | 03/023824 A2 | 3/2003 |
| WO | 03/036290 A1 | 5/2003 |
| WO | 2004/058837 A2 | 7/2004 |
| WO | 2004/100666 A1 | 11/2004 |
| WO | 2007/024393 A2 | 3/2007 |
| WO | 2007/068744 A1 | 6/2007 |
| WO | 2007/099239 A2 | 9/2007 |
| WO | 2007/127512 A2 | 11/2007 |
| WO | 2008/019381 A1 | 2/2008 |
| WO | 2008/061223 A3 | 5/2008 |
| WO | 2008/083390 A2 | 7/2008 |
| WO | 2008/122793 A2 | 10/2008 |
| WO | WO2008122793 | * 10/2008 |
| WO | 2009/014553 A1 | 1/2009 |
| WO | 2009/025680 A1 | 2/2009 |
| WO | 2009/067562 A1 | 5/2009 |
| WO | 2009/067565 A2 | 5/2009 |
| WO | 2009/067566 A1 | 5/2009 |
| WO | 2009/076323 A2 | 6/2009 |
| WO | 2009/076323 A3 | 6/2009 |
| WO | 2009/136869 A1 | 11/2009 |
| WO | 2010/030251 A2 | 3/2010 |
| WO | 2010/033435 A2 | 3/2010 |
| WO | 2010/062627 A2 | 6/2010 |
| WO | WO2010/062627 | * 6/2010 |
| WO | 2010/120293 A1 | 10/2010 |
| WO | 2011/057219 A2 | 5/2011 |
| WO | 2011/057224 A2 | 5/2011 |
| WO | 2011/057225 A2 | 5/2011 |
| WO | 2011/088247 A1 | 7/2011 |
| WO | 2011/133670 A2 | 10/2011 |
| WO | 2011/152747 A1 | 12/2011 |
| WO | 2012/061778 A2 | 5/2012 |
| WO | 2012/061778 A3 | 5/2012 |
| WO | 2012/149497 A2 | 11/2012 |

OTHER PUBLICATIONS

Brault, N.D., et al., "Ultra-Low Fouling and Functionalizable Zwitterionic Coatings Grafted Onto SiO2 Via a Biomimetic Adhesive Group for Sensing and Detection in Complex Media," Biosensors and Bioelectronics 25(10):2276-2282, Jun. 2010.

European Search Report dated Feb. 12, 2015, issued in European Application No. 12814998.6, filed Jul. 20, 2012, 10 pages.

Gohring, J.T., et al., "Label Free Detection of CD4+ and CD8+ T Cells Using the Optofluidic Ring Resonator," Sensors 10(6):5798-5808, Jun. 2010.

Canadian Office Action and Examination Search Report, mailed Dec. 12, 2014, issued in Canadian Application No. 2,872,378, filed Jul. 20, 2012, 3 pages.

Singh, N., et al., "The Role of Independently Variable Grafting Density and Layer Thickness of Polymer Nanolayers on Peptide Adsorption and Cell Adhesion," Biomaterials 28(5):763-761, Feb. 2007.

Spisak, S., et al., "Protein Microchips in Biomedicine and Biomarker Discovery," Electrophoresis 28(23):4261-4273, Dec. 2007.

Sun, R., et al., "Horizontal Single and Multiple Slot Waveguides: Optical Transmission at $\lambda=$ 1550 nm," Optics Express 15(26):17967-17972, Dec. 2007.

Tanabe, T., et al., "Trapping and Delaying Photons for One Nanosecond in an Ultrasmall High-Q Photonic-Crystal Nanocavity," Nature Photonics 1(1):49-52, Jan. 2007.

(56) References Cited

OTHER PUBLICATIONS

Thomas, W., "Catch Bonds in Adhesion," Annual Review of Biomedical Engineering 10:39-57, Aug. 2008.
Toomey, R., and M. Tirrell, "Functional Polymer Brushes in Aqueous Media From Self-Assembled and Surface-Initiated Polymers," Annual Review of Physical Chemistry 59:493-517, May 2008.
Tsai, W.-B., et al., "Human Plasma Fibrinogen Adsorption and Platelet Adhesion to Polystyrene," Journal of Biomedical Materials Research 44(2):130-139, Feb. 1999.
Turgman-Cohen, S., and J. Genzer, "Computer Simulation of Controlled Radical Polymerization: Effect of Chain Confinement Due to Initiator Grafting Density and Solvent Quality in 'Grafting From' Method," Macromolecules 43(22):9567-9577, Nov. 2010.
Vaisocherová, H., et al., "Functionalizable Surface Platform With Reduced Nonspecific Protein Adsorption From Full Blood Plasma—Material Selection and Protein Immobilization Optimization," Biosensors and Bioelectronics 24(7):1924-1930, Mar. 2009.
Vollmer, F., et al., "Multiplexed DNA Quantification by Spectroscopic Shill of Two Microsphere Cavities," Biophysical Journal 85(3):1974-1979, Sep. 2003.
Vollmer, F., et al., "Protein Detection by Optical Shift of a Resonant Microcavity," Applied Physics Letters 80(21):4057-4059, May 2002.
Von Muhlen, M.G., et al., "Label-Free Biomarker Sensing in Undiluted Serum With Suspended Microchannel Resonators," Analytical Chemistry 82(5):1905-1910, Mar. 2010.
Vörös, J., "The Density and Refractive Index of Adsorbing Protein Layers," Biophysical Journal 87(1):553-561, Jul. 2004.
Wang, D., et al., "Carbohydrate Microarrays for the Recognition of Cross-Reactive Molecular Markers of Microbes and Host Cells," Nature Biotechnology 20(3):275-281, Mar. 2002.
Wang, H., et al., "Probing the Orientation of Surface-Immobilized Immunoglobulin G by Time-of-Flight Secondary Ion Mass Spectrometry." Langmuir 20(5):1877-1887, Jan. 2004.
Wang, X., et al., "Length Scale Heterogeneity in Lateral Gradients of Poly(N-isopropylacrylamide) Polymer Brushes Prepared by Surface-Initiated Atom Transfer Radical Polymerization Coupled With In-Plane Electrochemical Potential Gradients," Langmuir 22(2):817-823, Jan. 2006.
Wang, Y., and M. Lieberman, "Growth of Ultrasmooth Octadecyltrichlorosilane Self-Assembled Monolayers on $SiO_2$," Langmuir 19(4):1159-1167, Jan. 2003.
Washburn, A.L., and R.C. Bailey, "Photonics-on-a-Chip: Recent Advances in Integrated Waveguides as Enabling Detection Elements for Real-World, Lab-on-a-Chip Biosensing Applications," Analyst 136(2):227-236, Jan. 2011.
West, S.L., et al., "The Biocompatibility of Crosslinkable Copolymer Coatings Containing Sulfobetaines and Phosphobetaines," Biomaterials 25(7-8):1195-1204, Mar.-Apr. 2004.
Wu, T., "Formation and Properties of Surface-Anchored Polymer Assemblies With Tunable Physico-Chemical Characteristics," doctoral dissertation, North Carolina State University, Raleigh, N.C., Mar. 2003, 205 pages.
Xiao, S.-J., et al., "Covalent Attachment of Cell-Adhesive Peptides Containing (Arg-Gly-Asp) Sequences to Titanium Surfaces," Langmuir 14(19):5507-5516, Aug. 1998.
Xu, Q., and M. Lipson, "All-Optical Logic Based on Silicon Micro-Ring Resonators," Optics Express 15(3):924-929, Feb. 2007.
Xu, Q., et al., "Breaking the Delay-Bandwidth Limit in a Photonic Structure," Nature Physics 3(6):406-410, Apr. 2007.
Xu, Q., et al., "Experimental Demonstration of Guiding and Confining Light in Nanometer-Size Low-Refractive-Index Material," Optics Letters 29(14):1626-1628, Jul. 2004.
Yang, W., et al., "Pursuing 'Zero' Protein Adsorption of Poly(carboxybetaine) From Undiluted Blood Serum and Plasma," Langmuir 25(19):11911-11916, Oct. 2009.
Yonzon, C.R., et al., "A Comparative Analysis of Localized and Propagating Surface Plasmon Resonance Sensors: The Binding of Concanavalin A to a Monosaccharide Functionalized Self-Assembled Monolayer," Journal of the American Chemical Society 126(39):12669-12676, Sep. 2004.
Yoshida, Y., et al., "Evidence of Chemical Bonding at Biomaterial-Hard Tissue Interfaces," Journal of Dental Research 79(2):709-714, Feb. 2000.
Yu, R.K., and M. Yanagisawa, "Glycobiology of Neural Stem Cells," CNAS & Neurological Disorders Drug Targets 5(4):415-423, Aug. 2006.
Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.
Yuan, J., et al., "Improvement of Blood Compatibility on Cellulose Membrane Surface by Grafting Betaines," Colloids and Surfaces B: Biointerfaces 30(1-2):147-155, Jul. 2003.
Yuan, J., et al., "Platelet Adhesion Onto Segmented Polyurethane Surfaces Modified by Carboxybetaine," Journal of Biomatenal Science, Polymer Edition 14(12):1339-1349, Dec. 2003.
Yuan, Y., et al., "Grafting Sulfobetaine Monomer Onto Silicone Surface to Improve Haemocompatibility," Polymer International 53(1):121-126, Jan. 2004.
Yuan, Y., et al., "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.
Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.
Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.
Zhang, F., and M.P. Srinivasan, "Multilayered Gold-Nanoparticle/Polyimide Composite Thin Film Through Layer-by-Layer Assembly," Langmuir 23(20):10102-10108, Aug. 2007.
Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.
Zhang, Z., et al., "Dual-Functional Biomimetic Materials: Nonfouling Poly(carboxybetaine) With Active Functional Groups for Protein Immobilization," Biomacromolecules 7(12):3311-3315, Dec. 2006.
Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.
Zhang, Z., et al., "Nonfouling Behavior of Polycarboxybetaine-Grafted Surfaces: Structural and Environmental Effects," Biomacromolecules 9(10):2686-2692, Oct. 2008.
Zhang, Z., et al., "Superlow Fouling Sulfobetaine and Carboxybetaine Polymers on Glass Slides," Langmuir 22(24):10072-10077, Nov. 2006.
Zhang, Z., Z., et al., "Surface Grafted Sulfobetaine Polymers via Atom Transfer Radical Polymerization as Superlow Fouling Coatings," Journal of Physical Chemistry B 110(22):10799-10804, Jun. 2006.
Zhao, C., et al., "Effect of Film Thickness on the Antifouling Performance of Poly(hydroxy-functional methacrylates) Grafted Surfaces," Langmuir 27(8):4906-4913, Apr. 2011.
Zhao, Y.-D., et al., "DNA-Modified Electrodes. Part 4: Optimization of Covalent Immobilization of DNA on Self-Assembled Monolayers," Talanta 49(4):751-756, Jul. 1999.
Zheng, J., et al., "Molecular Simulation Study of Water Interactions With Oligo (Ethylene Glycol)-Terminated Alkanethiol Self-Assembled Monolayers," Langmuir 20(20):8931-8938, Sep. 2004.
Zheng, J., et al., "Strong Repulsive Forces Between Protein and Oligo (Ethylene Glycol) Self-Assembled Monolayers: A Molecular Simulation Study," Biophysical Journal 89(1):158-166, Jul. 2005.
Zhou, J., et al., "Platelet Adhesion and Protein Adsorption on Silicone Rubber Surface by Ozone-Induced Grafted Polymerization With Carboxybetaine Monomer," Colloids and Surfaces B: Biointerfaces 41(1):55-62, Mar. 2005.
Zhu, H., et al., "Opto-Fluidic Micro-Ring Resonator for Sensitive Label-Free Viral Detection," Analyst 133(3):356-360, Mar. 2008.

(56) References Cited

OTHER PUBLICATIONS

Léonard, D., et al., "ToF-SIMS and XPS Study of Photoactivatable Reagents Designed for Surface Glycoengineering. Part III. 5-Carboxamidopentyl-N-[m-[3-(trifluoromethyl)diazirin-3-yl]phenyl-β-D-galactopyranosyl]-(1->4            )-1-thio-β-D-glucopyranoside (Lactose Aryl Diazirine) on Diamond," Surface and Interface Analysis 31(6):457-464, Jun. 2001.

Li, L., et al., "Harnessing Optical Forces in Integrated Photonic Circuits," Nature 456(7221):480-484, Nov. 2008.

Li, L., et al., "Protein Adsorption on Alkanethiolate Self-Assembled Monolayers: Nanoscale Surface Structural and Chemical Effects," Langmuir 19(7):2974-2982, Apr. 2003.

Li, L., et al., "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.

Li, L., et al., "Protein Interactions With Oligo(ethylene glycol) (OEG) Self-Assembled Monolayers: OEG Stability, Surface Packing Density and Protein Adsorption," Journal of Biomaterials Science, Polymer Edition 18(11):1415-1427, 2007.

Limpoco, F.T., and R.C. Bailey, "Real-Time Monitoring of Surface-Initiated Atom Transfer Radical Polymerization Using Silicon Photonic Microring Resonators: Implications for Combinatorial Screening of Polymer Brush Growth Conditions," Journal of the American Chemical Society 133(38):14864-14867, Sep. 2011.

Liotta, L.A., et al., "Protein Microarrays: Meeting Analytical Challenges for Clinical Applications," Cancer Cell 3(4):317-325, Apr. 2003.

Liu, A., et al., "A High-Speed Silicon Optical Modulator Based on a Metal-Oxide-Semiconductor Capacitor," Nature 427(6975):615-618, Feb. 2004.

Liu, A., et al., "Optical Amplification and Lasing by Stimulated Raman Scattering in Silicon Waveguides," IEEE Journal of Lightwave Technology 24(3):1440-1455, Mar. 2006.

Liu, J., et al., "Design of Monolithically Integrated GeSi Electroabsorption Modulators and Photodetectors on an SOI Platform," Optics Express 15(2):623-628, Jan. 2007.

Löfås, S., and B. Johnsson, "A Novel Hydrogel Matrix on Gold Surfaces in Surface Plasmon Resonance Sensors for Fast and Efficient Covalent Immobilization of Ligands," Journal of the Chemical Society, Chemical Communications 21:1526-1528, 1990.

Löfås, S., et al., "Methods for Site Controlled Coupling to Carboxymethyldextran Surfaces in Surface Plasmon Resonance Sensors," Biosensors & Bioelectronics 10(9-10):813-822, 1995.

Lowe, A.B., et al., "Well-Defined Sulfobetaine-Based Statistical Copolymers as Potential Antibioadherent Coatings," Journal of Biomedical Materials Research 52(1):88-94, Jul. 2000.

Luo, N., et al., "A Methacrylated Photoiniferter as a Chemical Basis for Microlithography: Micropatterning Based on Photografting Polymerization," Macromolecules 36(18):6739-6745, Sep. 2003.

Masson, J.-F., et al., "Biocompatible Polymers for Antibody Support on Gold Surfaces," Talanta 67(5):918-925, Oct. 2005.

Matsuda, T., "Photoiniferter-Driven Precision Surface Graft Microarchitectures for Biomedical Applications," in R. Jordan (ed.), "Surface-Initiated Polymerization I," Springer: Berlin, Advanced Polymeric Science 197:67-106, 2006.

Matyjaszewski, K., and N.V. Tsarevsky, "Nanostructured Functional Materials Prepared by Atom Transfer Radical Polymerization," Nature Chemistry 1(4):276-288, Jul. 2009.

Matyjaszewski, K., et al., "Polymers at Interfaces: Using Atom Transfer Radical Polymerization in the Controlled Growth of Homopolymers and Block Copolymers From Silicon Surfaces in the Absence of Untethered Sacrificial Initiator," Macromolecules 32(26):8716-8724, Dec. 1999.

Mendelsohn, J.D., et al., "Fabrication of Microporous Thin Films From Polyelectrolyte Multilayers," Langmuir 16(11):5017-5023, May 2000.

Midwood, K.S., et al., "Easy and Efficient Bonding of Biomolecules to an Oxide Surface of Silicon," Langmuir 20(13):5501-5505, May 2004.

"Nail Infections," Health 911, <http://www.health911.com/nail-infections> [retrieved Aug. 29, 2011], 3 pages.

Noto, M., et al., "Detection of Protein Orientation on the Silica Microsphere Surface Using Transverse Electric/Transverse Magnetic Whispering Gallery Modes," Biophysical Journal 92(12):4466-4472, Jun. 2007.

Ostuni, E., et al., "Self-Assembled Monolayers That Resist the Adsorption of Proteins and the Adhesion of Bacterial and Mammalian Cells," Langmuir 17(20):6336-6343, Oct. 2001.

Ostuni, E., "A Survey of Structure-Property Relationships of Surfaces That Resist the Adsorption of Protein," Langmuir 17(18):5605-5620, Sep. 2001.

Otsu, T., "Iniferter Concept and Living Radical Polymerization," Journal of Polymer Science: Part A: Polymer Chemistry 38(12):2121-2136, Jun. 2000.

Otsu, T., and M. Yoshida, "Role of Initiator-Transfer Agent-Terminator (Iniferter) in Radical Polymerizations: Polymer Design by Organic Disulfides as Iniferters," Die Makromolekulare Chemie, Rapid Communications (Macromolecular Rapid Communications) 3(2):127-132, Feb. 1982.

Otsuka, H., et al., "PEGylated Nanoparticles for Biological and Pharmaceutical Applications," Advanced Drug Delivery Reviews 55(3):403-419, Feb. 2003.

Prime, K.L., and G.M. Whitesides, "Self-Assembled Organic Monolayers: Model Systems for Studying Adsorption of Proteins at Surfaces," Science 252(5009):1164-1167, May 1991.

Pyun, J., et al., "Synthesis of Polymer Brushes Using Atom Transfer Radical Polymerization," Macromolecular Rapid Communications 24(18):1043-1059, Dec. 2003.

Quan, Q., et al., "Photonic Crystal Nanobeam Cavity Strongly Coupled to the Feeding Waveguide," Applied Physics Letters 96(20):203102-1-203102-3, May 2010.

Rahane, S.B., et al., "Impact of Added Tetraethylthiuram Disulfide Deactivator on the Kinetics of Growth and Reinitiation of Poly(methyl methacrylate) Brushes Made by Surface-Initiated Photoiniferter-Mediated Photopolymerization," Macromolecules 39(26):8987-8991, Dec. 2006.

Rahane, S.B., et al., "Kinetic Modeling of Surface-Initiated Photoiniferter-Mediated Photopolymerization in Presence of Tetraethylthiuram Disulfide," Macromolecules 41(24):9612-9618, Dec. 2008.

Rahane, S.B., et al., "Kinetics of Surface-Initiated Photoiniferter-Mediated Photopolymerization," Macromolecules 38(20):8202-8210, Oct. 2005.

Ramachandran, A., et al., "A Universal Biosensing Platform Based on Optical Micro-Ring Resonators," Biosensors and Bioelectronics 23(7):939-944, Feb. 2008.

Ratner B.D., and S.J. Bryant, "Biomaterials: Where We Have Been and Where We Are Going," Annual Review of Biomedical Engineering 6:41-75, Aug. 2004.

Ratner, D.M., et al., "Probing Protein-Carbohydrate Interactions With Microarrays of Synthetic Oligosaccharides," ChemBioChem 5(3):379-383, Mar. 2004.

Ratner, D.M., et al., "Tools for Glycomics: Mapping Interactions of Carbohydrates in Biological Systems," ChemBioChem 5(10):1375-1383, Oct. 2004.

Rodriguez-Emmenegger, C., et al., "Polymer Brushes Showing Non-Fouling in Blood Plasma Challenge the Currently Accepted Design of Protein Resistant Surfaces," Macromolecular Rapid Communications 32(13):952-957, Jul. 2011.

Roelkens, G., et al., "Efficient Silicon-on-Insulator Fiber Coupler Fabricated Using 248-nm-Deep UV Lithography," IEEE Photonics Technology Letters 17(12):2613-2615, Dec. 2005.

Roelkens, G., et al., "High Efficiency Grating Coupler Between Silicon-on-Insulator Waveguides and Perfectly Vertical Optical Fibers," Optics Letters 32(11):1495-1497, Jun. 2007.

Rong, H., et al., "An All-Silicon Raman Laser," Nature 433(7023):292-294, Jan. 2005.

Sabbatini, L., and P.G. Zambonin, "XPS and SIMS Surface Chemical Analysis of Some Important Classes of Polymeric Biomaterials," Journal of Electron Spectroscopy and Related Phenomena 81(3):285-301, Sep. 1996.

(56) References Cited

OTHER PUBLICATIONS

Sacchettini, J.C., et al., "Multivalent Protein-Carbohydrate Interactions. A New Paradigm for Supermolecular Assembly and Signal Transduction," Biochemistry 40(10):3009-3015, Mar. 2001.

Salminen, A., et al., "Inhibition of P-Fimbriated *Escherichia coli* Adhesion by Multivalent Galabiose Derivatives Studied by a Live-Bacteria Application of Surface Plasmon Resonance," Journal of Antimicrobial Chemotherapy 60(3):495-501, Sep. 2007.

Sauer, U., et al., "Evaluation of Substrate Performance for a Microbial Diagnostic Microarray Using a Four Parameter Ranking," Analytica Chimica Acta 632(2):240-246, Jan. 2009.

Schmidt, B., et al., "Optical Trapping Platform Based on Highly Confining Silicon Waveguiding Structures With Microfluidics," Conference on Lasers and Electro-Optics and Conference on Quantum Electronics and Laser Science (CLEO/QELS), San Jose, Calif., May 4-9, 2008, OSA Technical Digest (CD), Optical Society of America, Paper CThQ3, 2 pages.

Schoen, F.J., and A.S. Hoffman, "Implant and Device Failure," in B.D. Ratner et al. (eds.), "Biomaterials Science," 2nd ed., Elsevier, Oxford, U.K., Chap. 9.3, pp. 760-765, 2004.

Shapiro, M.G., et al., "Directed Evolution of a Magnetic Resonance Imaging Contrast Agent for Noninvasive Imaging of Dopamine," Nature Biotechnology 28(3):264-270, Mar. 2010.

Sherwood-Droz, N., et al., "Optical 4×4 Hitless Silicon Router for Optical Networks-on-Chip (NoC)," Optics Express 16(20):15915-15922, Sep. 2008.

Silverman, B.M., et al., "Comparative Properties of Siloxane vs. Phosphonate Monolayers on a Key Titanium Alloy," Langmuir 21(1):225-228, Jan. 2005.

European Office Action and Examination Search Report, mailed Nov. 20, 2015, issued in European Application No. 12 814 998.6, filed Jul. 20, 2012, 7 pages.

Communication Pursuant to Article 94(3) EPC mailed Nov. 20, 2015, issued in corresponding European Application No. 12 814 998.6, filed Jul. 20, 2012, 7 pages.

Final Office Action mailed Sep. 22, 2015, from U.S. Appl. No. 13/747,290, filed Jan. 22, 2013, 20 pages.

Gohring, J.T., and X. Fan, "Label Free Detection of CD4+ and CD8+ T Cells Using the Optofluidic Ring Resonator," Sensors 10(6):5798-5808, Jun. 2010.

Adams, E.W., et al., "Oligosaccharide and Glycoprotein Microarrays as Tools in HIV-Glycobiology: A Detailed Analysis of Glycan Dependent gp120/Protein Interactions," Chemistry & Biology 11(6):875-881, Jun. 2004.

Adden, N., et al., "Phosphonic Acid Monolayers for Binding of Bioactive Molecules to Titanium Surfaces," Langmuir 22(19):8197-8204, Aug. 2006.

Almeida, V.R., et al., "Guiding and Confining Light in Void Nanostructure," Optics Letters 29(11):1209-1211, Jun. 2004.

Almeida, V.R., et al., "Nanotaper for Compact Mode Conversion," Optics Letters 28(15):1302-1304, Aug. 2003.

Anderson, J. M., "Inflammation, Wound Healing, and the Foreign-Body Response," in B.D. Ratner et al. (eds.), "Biomaterials Science: an Introduction to Materials in Medicine," 2nd ed., Elsevier, Oxford, U.K., pp. 296-304,2004.

Aprikian, P., et al., "Interdomain Interaction in the FimH Adhesin of *Escherichia coli* Regulates the Affinity to Mannose," Journal of Biological Chemistry 282(32):23437-23446, Aug. 2007.

Armani, A.M., et al., "Label-Free, Single-Molecule Detection With Optical Microcavities," Science 317(5839):783-787, Aug. 2007.

Aspnes, D.E., "Optical Properties of Thin Films," Thin Solid Films 89(3):249-262, Mar. 1982.

Azzaroni, O., et al., "UCST Wetting Transitions of Polyzwitterionic Brushes Driven by Self-Association," Angewandte Chemie International Edition 45(11)1770-1774, Mar. 2006.

Baehr-Jones, T., et al., "High-Q Ring Resonators in Thin Silicon-on-Insulator," Applied Physics Letters 85(16):3346-3347, Oct. 2004.

Baehr-Jones, T., et al., "Nonlinear Polymer-Clad Silicon Slot Waveguide Modulator With a Half Wave Voltage of 0.25 V," Applied Physics Letters 92(16):163303-1-163303-3, Apr. 2008.

Baehr-Jones, T., et al., "Optical Modulation and Detection in Slotted Silicon Waveguides," Optics Express 13(14):5216-5226, Jul. 2005.

Berge, S.M., et al., "Pharmaceutical Salts," Journal of Pharmaceutical Sciences 66(1):1-19, Jan. 1977.

"Betaine," Wikipedia, The Free Encyclopedia, <http://en.wikipedia.org/wiki/Betaine> [retrieved Jul. 31, 2011], 1 page.

Boyraz, O., and B. Jalali, "Demonstration of a Silicon Raman Laser," Optics Express 12(21):5269-5273, Oct. 2004.

Braunecker, W.A., and K. Matyjaszewski, "Controlled/Living Radical Polymerization: Features, Developments, and Perspectives," Progress in Polymer Science 32(1):93-146, Jan. 2007.

"Bromide," Wikipedia, The Free Encyclopedia, <http://en.wikipedia.org/wiki/Bromide> [retrieved Jul. 27, 2011], 3 pages.

Browne, M.M., "Protein Adsorption Onto Polystyrene Surfaces Studied by XPS and AFM," Surface Science 553(1-3):155-167, Mar. 2004.

Callow, J.A., and M.E. Callow, "Trends in the Development of Environmentally Friendly Fouling-Resistant Marine Coatings," Nature Communications 2:244, Mar. 2011, 10 pages.

Calvo, K.R., et al., "Clinical Proteomics: From Biomarker Discovery and Cell Signaling Profiles to Individualized Personal Therapy," Bioscience Reports 25(1-2):107-125, Feb.-Apr. 2005.

Castner, D.G., and B.D. Ratner, "Biomedical Surface Science: Foundations to Frontiers," Surface Science 500(1-3):28-60, Mar. 2002.

Cattani-Scholz, A., et al., "Organophosphonate-Based PNA-Functionalization of Silicon Nanowires for Label-Free DNA Detection," ACS Nano 2(8):1653-1660, Jul. 2008.

Chang, Y., et al., "Highly Protein-Resistant Coatings From Well-Defined Diblock Copolymers Containing Sulfobetaines," Langmuir 22(5):2222-2226, Feb. 2006.

Chao, C.-Y., et al., "Polymer Microring Resonators for Biochemical Sensing Applications," IEEE Journal of Selected Topics in Quantum Electronics 12(1):134-142, Jan.-Feb. 2006.

Chen, S., et al., "Controlling Antibody Orientation on Charged Self-Assembled Monolayers," Langmuir 19(7):2859-2864, Apr. 2003.

Chen, S., et al., "Strong Resistance of Oligio(phosphorylcholine) Self-Assembled Monolayers to Protein Adsorption," Langmuir 22(6):2418-2421, Mar. 2006.

Chen, S., et al., "Strong Resistance of Phosphorylcholine Self-Assembled Monolayers to Protein Adsorption: Insights Into Nonfouling Properties of Zwitterionic Materials," Journal of the American Chemical Society 127(41):14473-14478, Oct. 2005.

Cheng, N., et al., "The Effect of [Cu(I)]/[Cu(II)] Ratio on the Kinetics and Conformation of Polyelectrolyte Brushes by Atom Transfer Radical Polymerization," Macromolecular Rapid Communications 27(19):1632-1636, Oct. 2006.

Coen, M.C., et al., "Adsorption and Bioactivity of Protein A on Silicon Surfaces Studied by AFM and XPS," Journal of Colloid and Interface Science 233(2):180-189, Jan. 2001.

Cook, A.D., et al., "Characterization and Development of RGD-Peptide-Modified Poly(lactic acid-co-lysine) as an Interactive, Resorbable Biomaterial," Journal of Biomedical Materials Research 35(4):513-523, Jun. 1997.

Crocker, P. R., et al., "Siglecs and Their Roles in the Immune System," Nature Reviews Immunology 7(4):255-266, Apr. 2007.

Davis, S.J., and J.F. Watts, "Interfacial Chemistry of Adhesive Joint Failure: An Investigation by Small Area XPS, Imaging XPS and TOF-SIMS," Journal of Materials Chemistry 6(3):479-493, Mar. 1996.

De Boer, B., et al., "'Living' Free Radical Photopolymerization Initiated From Surface-Grafted Iniferter Monolayers," Macromolecules 33(2):349-356, Jan. 2000.

De Vos, K., et al., "Silicon-on-Insulator Microring Resonator for Sensitive and Label-Free Biosensing," Optics Express 15(12):7610-7615, Jun. 2007.

Deng, J., et al., "Developments and New Applications of UV-Induced Surface Graft Polymerizations," Progress in Polymer Science 34(2):156-193, 2009.

(56) References Cited

OTHER PUBLICATIONS

Dhayal, M., and D.M. Ratner, "XPS and SPR Analysis of Glycoarray Surface Density," Langmuir 25(4):2181-2187, Jan. 2009.
Disney, M.D., and P.H. Seeberger, "Aminoglycoside Microarrays to Explore Interactions of Antibiotics With RNAs and Proteins," Chemistry 10(13):3308-3314, Jul. 2004.
Disney, M.D., and P.H. Seeberger, "The Use of Carbohydrate Microarrays to Study Carbohydrate-Cell Interactions and to Detect Pathogens," Chemistry & Biology 11(12):1701-1707, Dec. 2004.
Dostálek, J., et al., "Surface Plasmon Resonance Biosensor Based on Integrated Optical Waveguide," Sensors and Actuators B 76(1-3):8-12, Jun. 2001.
Dufrêne, Y.F, et al., "X-Ray Photoelectron Spectroscopy Analysis of Whole Cells and Isolated Cell Walls of Gram-Positive Bacteria: Comparison With Biochemical Analysis," Journal of Bacteriology 179(4):1023-1028, Feb. 1997.
Edmondson, S., et al., "Surface Polymerization From Planar Surfaces by Atom Transfer Radical Polymerization Using Polyelectrolytic Macroinitiators," Macromolecules 40(15):5271-5278, Jul. 2007.
Eisenstein, M., "Protein Arrays: Growing Pains," Nature 444(7121):959-962, Dec. 2006.
Eskin, S.G., et al., "Some Background Concepts," in B.D. Ratner et al. (eds.), "Biomaterials Science," 2nd ed., Elsevier, Oxford, U.K., pp. 237-246, 2004.
Fan, X. et al., "Overview of Novel Integrated Optical Ring Resonator Bio/Chemical Sensors," Proceedings of SPIE 6452:64520M-1-64520M-20, Feb. 2007.
Fang, A.W., et al., "Electrically Pumped Hybrid AlGaInAs-Silicon Evanescent Laser," Optics Express 14(20):9203-9210, Oct. 2006.
Farokhzad, O.C., and R. Langer, "Impact of Nanotechnology on Drug Delivery," ACS Nano 3(1):16-20, 2009.
Fathpour, S., et al., "Energy Harvesting in Silicon Raman Amplifiers," Applied Physics Letters 89:061109-1-061109-3, Aug. 2006.
Feng, W., et al., "Adsorption of Fibrinogen and Lysozyme on Silicon Grafted With Poly(2-methacryloyloxyethyl Phosphorylcholine) via Surface-Initiated Atom Transfer Radical Polymerization," Langmuir 21(13):5980-5987, Jun. 2005.
Feng, W., et al., "Atom-Transfer Radical Grafting Polymerization of 2-Methacryloyloxyethyl Phosphorylcholine From Silicon Wafer Surfaces," Journal of Polymer Science: Part A: Polymer Chemistry 42(12):2931-2942, Jun. 2004.
Figeys, D., "Adapting Arrays and Lab-on-a-Chip Technology for Proteomics," Proteomics 2(4):373-382, Apr. 2002.
Foster, M.A., et al., "Broad-Band Optical Parametric Gain on a Silicon Photonic Chip," Nature 441(7096):960-963, Jun. 2006.
Fukui, S., et al., "Oligosaccharide Microarrays for High-Throughput Detection and Specificity Assignments of Carbohydrate-Protein Interactions," Nature Biotechnology 20(10):1011-1017, Oct. 2002.
Gawalt, E.S., et al., "Bonding Organics to Ti Alloys: Facilitating Human Osteoblast Attachment and Spreading on Surgical Implant Materials," Langmuir 19(1):200-204, Jan. 2003.
Goda, T., et al., "Biomimetic Phosphorylcholine Polymer Grafting From Polydimethylsiloxane Surface Using Photo-Induced Polymerization," Biomaterials 27(30):5151-5160, Oct. 2006.
Gong, P., et al., "Hybridization Behavior of Mixed DNA/Alkylthiol Monolayers on Gold: Characterization by Surface Plasmon Resonance and $^{32}$P Radiometric Assay," Analytical Chemistry 78(10):3326-3334, May 2006.
Gunn, C., "CMOS Photonics™ Technology: Enabling Optical Interconnects," Luxtera, Inc., Jan. 2012, <http://www.hotchips.org/archives/hc17/2_Mon/HC17.S3/HC17.S3T1.pdf> [retrieved Sep. 2015], 26 pages.
Guo, Y., et al., "Structural Basis for Distinct Ligand-Binding and Targeting Properties of the Receptors DC-SIGN and DC-SIGNR," Nature Structural & Molecular Biology 11(7):591-598, Jul. 2004.
Hanson, E.L., et al., "Bonding Self-Assembled, Compact Organophosphonate Monolayers to the Native Oxide Surface of Silicon," Journal of the American Chemical Society 125(51):16074-16080, Nov. 2003.

Harder, P., et al., "Molecular Conformation in Oligo(ethylene glycol)-Terminated Self-Assembled Monolayers on Gold and Silver Surfaces Determines Their Ability to Resist Protein Adsorption," Journal of Physical Chemistry B 102(2):426-436, Jan. 1998.
He, Y., et al., "Molecular Simulation Studies of Protein Interactions With Zwitterionic Phosphorylcholine Self-Assembled Monolayers in the Presence of Water," Langmuir 24(18):10358-10364, Sep. 2008.
Herne, T.M., and M.J. Tarlov, "Characterization of Probe Immobilized on Gold Surface," Journal of the American Chemical Society 119(38):8916-8920, Sep. 1997.
Hess, J.R., and J.B. Holcomb, "Transfusion Practice in Military Trauma," Transfusion Medicine 18(3):143-150, Jun. 2008.
Hochberg, M., et al., "Terahertz All-Optical Modulation in a Silicon-Polymer Hybrid System," Nature Materials 5(9):703-709, Sep. 2006.
Holcomb, J.B., "Optimal Use of Blood Products in Severely Injured Trauma Patients," Hematology 2010(1):465-469, Dec. 2010.
Holmlin, R.E., et al., "Zwitterionic SAMs That Resist Nonspecific Adsorption of Protein From Aqueous Buffer," Langmuir 17(9):2841-2850, May 2001.
Hölzl, M., et al., "Protein-Resistant Self-Assembled Monolayers on Gold With Latent Aldehyde Functions," Langmuir 23(10):5571-5577, May 2007.
Homola, J., "Electromagnetic Theory of Surface Plasmons," in O.S. Wolfbeis (ed.), "Surface Plasmon Resonance Based Sensors," Springer-Verlag: Berlin 4:3-44, 2006.
Homola, J., and M. Piliarik, "Surface Plasmon Resonance (SPR) Sensors," in O.S. Wolfbeis (ed.), "Surface Plasmon Resonance Based Sensors," Springer-Verlag: Berlin 4:45-67, 2006.
Homola, J., et al., "A Novel Multichannel Surface Plasmon Resonance Biosensor," Sensors and Actuators B: Chemical 76(1-3):403-410, Jun. 2001.
Houseman, B.T., and M. Mrksich, "Carbohydrate Arrays for the Evaluation of Protein Binding and Enzymatic Modification," Chemistry & Biology 9(4):443-454, Apr. 2002.
Houseman, B.T., et al., "Maleimide-Functionalized Self-Assembled Monolayers for the Preparation of Peptide and Carbohydrate Biochips," Langmuir 19(5):1522-1531, Mar. 2003.
Hoyle, C.E., and C.N. Bowman, "Thiol—Ene Click Chemistry," Angewandte Chemie International Edition 49(9):1540-1573, Feb. 2010.
Huang, C.-J., et al., "Long-Range Surface Plasmon-Enhanced Fluorescence Spectroscopy Biosensor for Ultrasensitive Detection of *E. coli* O157:H7," Analytical Chemistry 83(3):674-677, Feb. 2011.
Huang, N.-P., et al., "Poly(L-lysine)-g-poly(ethylene glycol) Layers on Metal Oxide Surfaces: Surface-Analytical Characterization and Resistance to Serum and Fibrinogen Adsorption," Langmuir 17(2):489-498, Jan. 2001.
Huang, R.-P., "Protein Arrays, an Excellent Tool in Biomedical Research," Frontiers in Bioscience 8:d559-576, May 2003.
Huang, W., et al., "Functionalization of Surfaces by Water-Accelerated Atom-Transfer Radical Polymerization of Hydroxyethyl Methacrylate and Subsequent Derivatization," Macromolecules 35(4):1175-1179, Feb. 2002.
Hucknall, A., et al., "In Pursuit of Zero: Polymer Brushes That Resist the Adsorption of Proteins," Advanced Materials 21(23):2441-2446, Jun. 2009.
International Preliminary Report on Patentability mailed May 8,2012, issued in related International Application No. PCT/US2010/055887, filed Nov. 8,2010,8 pages.
International Search Report and Written Opinion mailed Jul. 28,2011, issued in related International Application No. PCT/US2010/055887, filed Nov. 8,2010, 12 pages.
Ishihara, K., et al., "Inhibition of Fibroblast Cell Adhesion on Substrate by Coating With 2-Methacryloyloxyethyl Phosphorylcholine Polymers," Journal of Biomedical Material Science, Polymer Edition 10(10):1047-1061, 1999.
Ishihara, K., et al., "Protein Adsorption From Human Plasma Is Reduced on Phospholipid Polymers," Journal of Biomedical Materials Research 25(11):1397-1407, Nov. 1991.

(56) References Cited

OTHER PUBLICATIONS

Jiang, S., and Z. Cao, "Ultralow-Fouling, Functionalizable, and Hydrolyzable Zwitterionic Materials and Their Derivatives for Biological Applications," Advanced Materials 22(9):920-932, Mar. 2010.

Jiang, Y., et al., "Blood Compatibility of Polyurethane Surface Grafted Copolymerization With Sulfobetaine Monomer," Colloids and Surfaces B: Biointerfaces 36(1):27-33, Jul. 2004.

Jones, D.M., et al., "Surface-Initiated Polymerizations in Aqueous Media: Effect of Initiator Density," Langmuir 18(4):1265-1269, Feb. 2002.

Joos, T.O., et al., "A Microarray Enzyme-Linked Immunosorbent Assay for Autoimmune Diagnostics," Electrophoresis 21(13):2641-2650, Jul. 2000.

Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.

Kansas, G.S., "Selectins and Their Ligands: Current Concepts and Controversies," Blood 88(9):3259-3287, Nov. 1996.

Karlsson, K.-A., "Bacterium-Host Protein-Carbohydrate Interactions and Pathogenicity," Biochemical Society Transactions 27(4):471-474, Aug. 1999.

Kastantin, M., and M. Tirrell, "Helix Formation in the Polymer Brush," Macromolecules 44(12):4977-4987, Jun. 2011.

Kim, B.-S., et al., "All-Star Polymer Multilayers as pH-Responsive Nanofilms," Macromolecules 42(1):368-375, Jan. 2009.

Kirk, J.T., et al., "Serologic and Phenotypic Analysis of Blood Types via Silicon Nanophotonics," Blood 124(21):1565-1565, Dec. 2014.

Kizhakkedathu, J.N., et al., "Poly(oligo(ethylene glycol)acrylamide) Brushes by Surface Initiated Polymerization: Effect of Macromonomer Chain Length on Brush Growth and Protein Adsorption From Blood Plasma," Langmuir 25(6):3794-3801, Mar. 2009.

Kolb, H.C., et al., "Click Chemistry: Diverse Chemical Function From a Few Good Reactions," Angewandte Chemie International Edition 40(11):2004-2021, Jun. 2001.

Krause, J.E., et al., "Photoiniferter-Mediated Polymerization of Zwitterionic Carboxybetaine Monomers for Low-Fouling and Functionalizable Surface Coatings," Macromolecules 44(23):9213-9220, Dec. 2011.

Ksendozov, A., and Y. Lin, "Integrated Optics Ring-Resonator Sensors for Protein Detection," Optics Letters 30(24):3344-3346, Dec. 2005.

Kumari, K., et al., "Receptor Binding Specificity of Recent Human H3N2 Influenza Viruses," Virology Journal 4:42, May 2007, 12 pages.

Ladd, J., et al., "Zwitterionic Polymers Exhibiting High Resistance to Nonspecific Protein Adsorption From Human Serum and Plasma," Biomacromolecules 9(5):1357-1361, May 2008.

Langer, R., "Drugs on Target," Science 293(5527):58-59, Jul. 2001.

Lee, B.S., et al., "Surface-Initiated, Atom Transfer Radical Polymerization of Oligo(ethylene glycol) Methyl Ether Methacrylate and Subsequent Click Chemistry for Bioconjugation," Biomacromolecules 8(2):744-749, Feb. 2007.

Lenigk, R., et al., "Surface Characterization of a Silicon-Chip-Based DNA Microarray," Langmuir 17(8):2497-2501, Mar. 2001.

International Search Report and Written Opinion mailed Jan. 30, 2013, issued in corresponding International Application No. PCT/US2012/047745, filed Jul. 20, 2012, 8 pages.

Summons to Attend Oral Proceedings mailed Jun. 27, 2016, issued in corresponding European Application No. 12 814 998.6, filed Jul. 20, 2012, 8 pages.

\* cited by examiner

PHOTONIC BLOOD TYPING

CROSS-REFERENCES TO RELATED APPLICATIONS

This application claims the benefit of U.S. Provisional Application No. 61/509,776, filed Jul. 20, 2011; and U.S. Provisional Application No. 61/588,785, filed Jan. 20, 2012, the disclosures of which are each expressly incorporated herein by reference in their entirety.

STATEMENT OF GOVERNMENT LICENSE RIGHTS

This invention was made with Government support under 0930411 and 1264174, awarded by the National Science Foundation, under HDTRA1-10-1-0074, awarded by the Defense Thread Reduction Agency, and under N000140910137, awarded by the Office of Naval Research. The Government has certain rights in the invention.

BACKGROUND

Recently, there has been a surge of interest in leveraging silicon photonics for biosensing, with the ultimate goal of producing a chip with thousands of orthogonal sensors capable of functioning in clinical environments and available at minimal cost. Silicon photonic biosensors have already achieved impressive sensitivities relevant for biomedical applications. However, the field has been stymied by the challenge of biological specificity, the ability to bind preferentially to an analyte of interest when sensing in complex biological samples (e.g., blood, plasma, serum). Here we show, for the first time on a silicon photonics platform, label-free biosensing with clinically relevant sensitivity in undiluted human serum. Utilizing a zwitterionic polymer-based surface chemistry, we dramatically limit the amount of non-specific protein adsorption to a microring resonator in serum, while maintaining a label-free sensitivity of 10 ng ml$^{-1}$. This result represents a significant step towards the practical application of silicon photonics for medical diagnostics and the biomedical sciences.

The noteworthy potential of silicon photonics emerges from the combination of excellent optical devices with control electronics to produce inexpensive integrated photonics systems. In recent years, on-chip modulators, detectors, and hybrid lasers have all been demonstrated. Microring resonators are exceedingly amenable to scalable fabrication using CMOS-compatible processes, setting them apart from most other resonant optical microcavity devices for high-throughput, multiplexed biosensing. To utilize the microring resonator for biological sensing, a binding site is chemically introduced on the surface of the sensor and a shift in the resonance wavelength of the microring is observed upon analyte binding. Exploiting this approach, SOI microring resonators have been used for the detection of a diverse range of biological species, including antibodies, proteins, nucleic acids, and bacteria, among others.

In evaluating a biosensor for a given application, there are two main figures of merit. First, the sensitivity of the device, and second, the complexity of the background solution in which the assay can be performed successfully. Many recent biosensing results have yielded excellent sensitivity, but in relatively simple solutions (low biological noise). FIG. 1A shows the distribution of attained sensitivities, as well as the biological noise in each demonstration. The suitability of these platforms for use in clinical assays depends not only on their sensitivity, but also on the selectivity of these sensors for a particular analyte in complex biological fluids (solutions with high biological noise).

For comparison, FIG. 1A includes the sensitivities of both colorimetric and chemiluminescent enzyme-linked immunosorbent assay (ELISA), the standard diagnostic technique used by most hospitals. Despite its widespread use and perceived effectiveness, the ELISA method is not without its limitations, as it requires signal amplification of bound analyte by primary and labeled secondary antibodies, substantially increasing both the cost and time of the diagnostic. A competing technology to ELISA, surface plasmon resonance (SPR), has also achieved low sensitivities in complex media. However, due to the complexity of plasmonic systems integration, SPR has not been realized as a highly-parallelized, portable, low-cost clinical assay. Also, while SPR is an effective label-free biosensing technology, the sensing range of SPR is limited, due to the exponential decay of the surface plasmon from the gold substrate. Thus, SPR is poorly suited to study targets, such as bacteria, where the size of the target places the majority of the refractive index change outside of the range of the evanescent wave. Therefore it would be desirable to develop a related label-free technology that could be used to sense targets at greater range from the surface of the device.

Ideally, a diagnostic test should require minimal processing of the biological sample prior to detection of the analyte of interest. However, non-specific adsorption of proteins in complex biological samples, a process known as fouling, significantly decreases the sensitivity of label-free devices due to a lack of biological specificity at the sensor surface. Common strategies for passivating surfaces to non-specific biological interactions include adsorption of 'blocking' proteins (e.g., serum albumin) and grafting inert polymeric scaffolds (e.g., polyethylene glycol) to the surface that increase surface hydration through intermolecular hydrogen bonding. These passivation strategies are only partially effective and are inadequate to fully resist protein fouling in complex biological samples.

One biological system of great interest is the typing of blood. Immediate bloody typing is not presently enabled by any simple, portable technologies. Blood typing is necessary for personalized treatment of wounds (e.g., in combat situations) and improved safety in blood banking.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a photonic device for determining blood type is provided. In one embodiment, the device includes:
  a sample waveguide having a sample surface; and
  a binding coating covering and being in optical communication with at least a portion of the sample surface, the binding coating being configured to bind a target moiety indicative of blood type, wherein the photonic device is configured such that light passed through the sample waveguide has an evanescent field that extends a distance beyond the sample waveguide sufficient to detect the target moiety indicative of blood type.

In another aspect, a photonic system for determining a blood type is provided. In one embodiment, the system includes:

(1) a first photonic device for determining the blood type, comprising:
   a first sample waveguide having a first sample surface; and
   a first binding coating covering and being in optical communication with at least a portion of the first sample surface, the first binding coating being configured to directly bind to a blood cell target moiety indicative of the blood type, wherein the blood cell target moiety is attached to a blood cell body selected from the group consisting of a blood cell, a blood cell membrane, a blood cell fragment, a microvesicle, and a blood cell-associated antigen, and wherein the first photonic device is configured such that light passed through the first sample waveguide has an evanescent field that extends a distance beyond the first sample waveguide sufficient to detect the bound blood cell target moiety; and
(2) a second photonic device for determining blood type, comprising:
   a second sample waveguide having a second sample surface; and
   a second binding coating covering and being in optical communication with at least a portion of the second sample surface, the second binding coating being configured to bind to an antibody or other acellular biological species indicative of the blood type, wherein the second photonic device is configured such that light passed through the second sample waveguide has an evanescent field that extends a distance beyond the second sample waveguide sufficient to detect the antibody indicative of the blood type.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Photonic devices, systems, and methods for detecting an analyte in a biological solution (e.g., whole blood) are provided. Representative photonic devices are optical ring resonators having nanoscale features and micron-sized diameters. Due to the compact size of these devices, many resonators can be disposed on a single substrate and tested simultaneously as a sample is passed over the devices. Typical analytes include blood cells, antibodies, and pathogens, as well as compounds indicative of the presence of blood cells, antibodies, or pathogens (e.g., serology). In certain embodiments, blood type or blood immune sensitization status can be determined through photonic sensing using a combination of direct detection of blood cells and serology. By combining the detection signals of multiple devices, the type of blood can be determined.

In one aspect, a photonic device for determining blood type or immune sensitization to blood type is provided. In one embodiment, the device includes:

a sample waveguide having a sample surface; and a binding coating covering and being in optical communication with at least a portion of the sample surface, the binding coating being configured to bind a target moiety indicative of blood type, wherein the photonic device is configured such that light passed through the sample waveguide has an evanescent field that extends a distance beyond the sample waveguide sufficient to detect the target moiety indicative of blood type.

In one embodiment, the binding coating has a first refractive index prior to binding the target moiety indicative of blood type and a second refractive index after binding the target moiety indicative of blood type, wherein the first refractive index and the second refractive index are different, and wherein an evanescent field of electromagnetic radiation of a first wavelength extends beyond the binding coating and into any binding moiety bound to the binding coating.

Figure 1A:
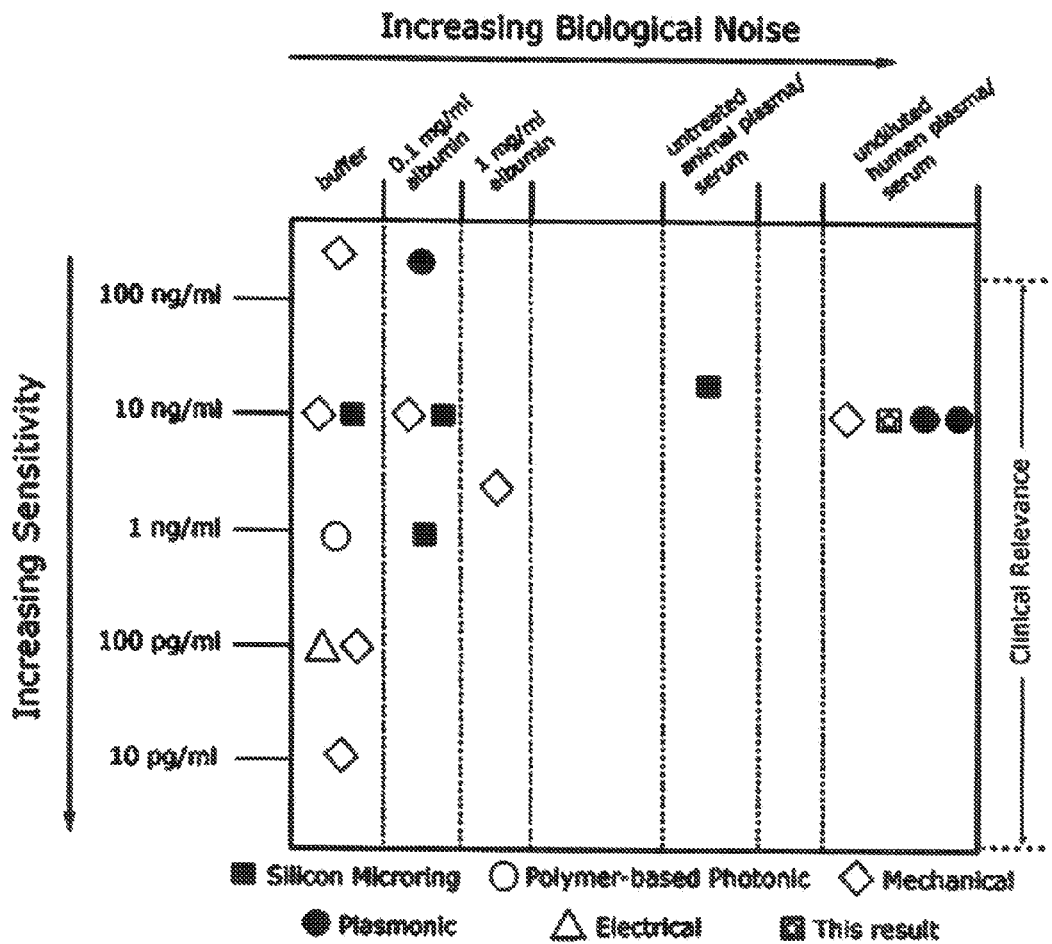
FIGS. 1A-1D. 1A: Distribution of achieved label-free sensitivities for plasmonic, mechanical, and photonic biosensors, as well as the levels of biological noise of the solutions tested. For comparison, the sensitivities of colorimetric and chemiluminescent ELISA assays are shown (dashed lines). 1B: Cross-section of the silicon with modal pattern indicated. Contours in |E| are plotted in 10% increments. 1C: Illustration of the biosensor array (left) and a scanning electron micrograph of a single microring resonator (right). 1D: Schematic illustration of the operation of photonic devices in accordance with the disclosed embodiments.
Figure 1B:
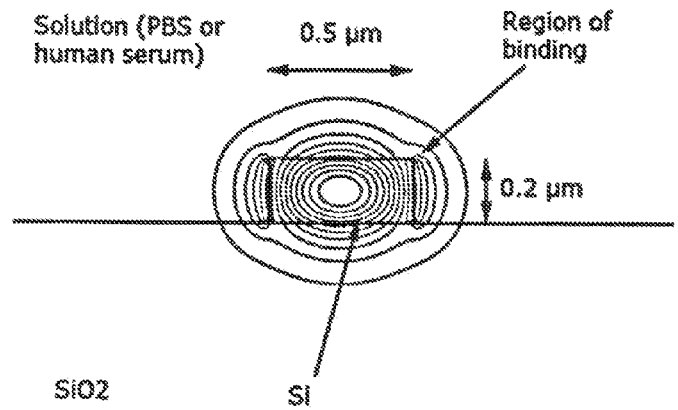
Figure 1C:
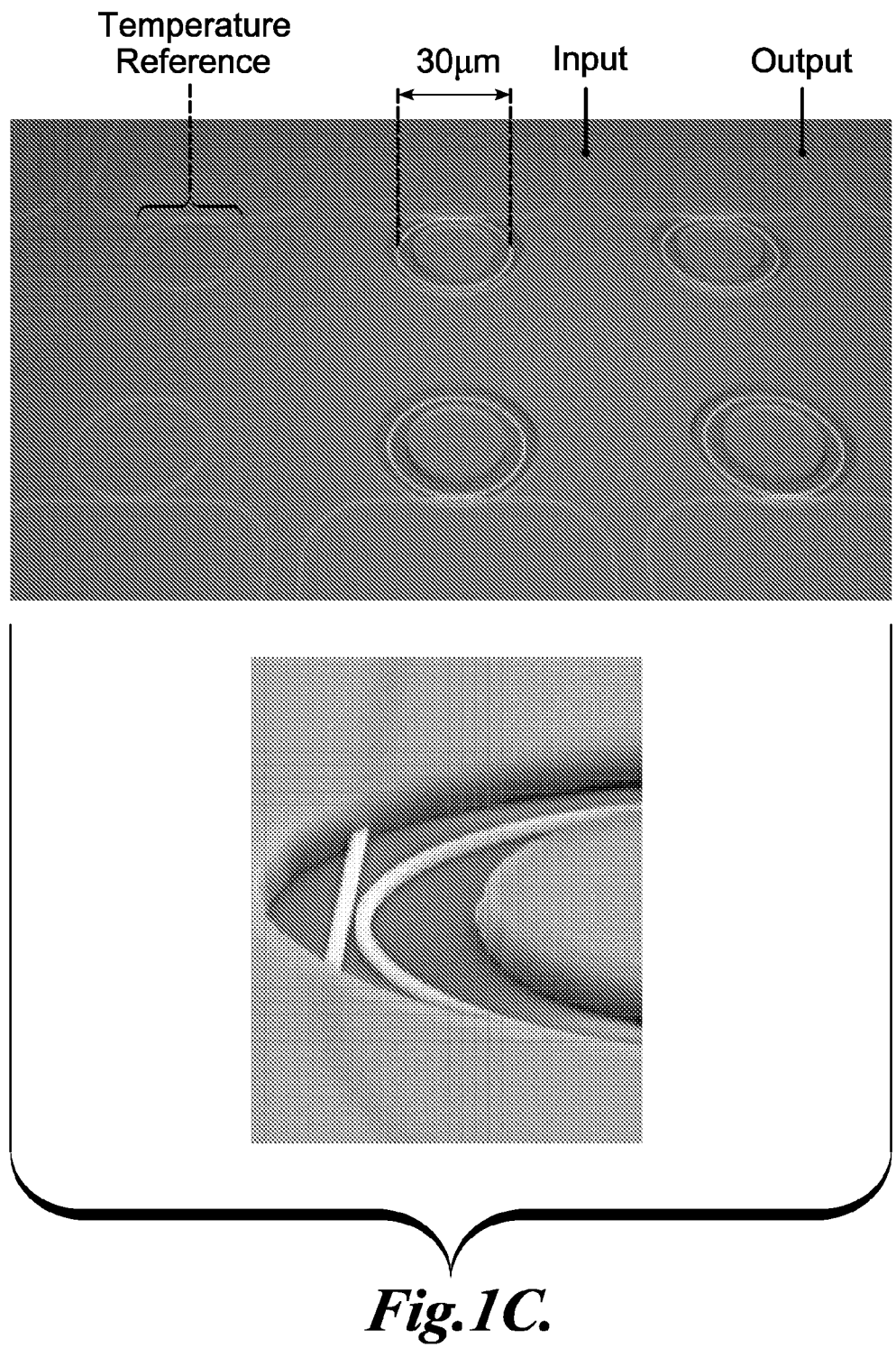
Figure 1D:
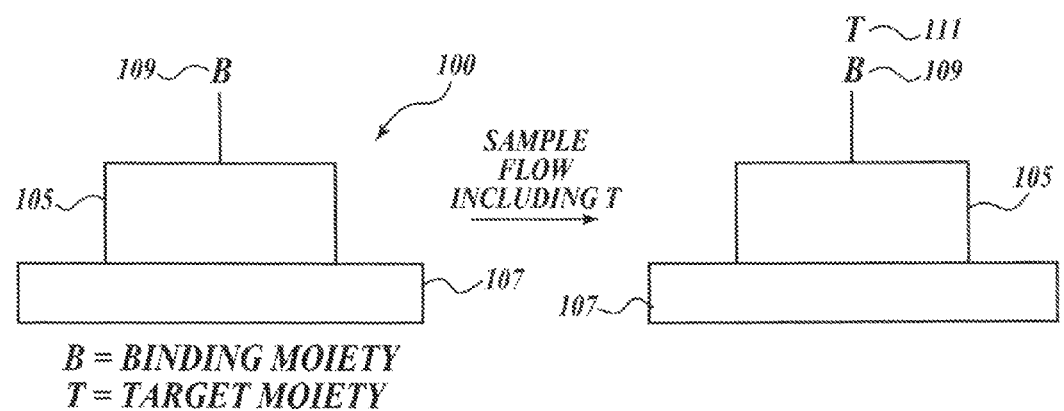

FIG. 1D illustrates a representative photonic device 100 used to capture a target moiety 111 from a biological sample fluid flowing over the device 100. The target moiety 111 is captured by a binding moiety 109 that is part of a binding coating coupled to a surface of a waveguide 105 such that the photonic device 100 is operable to detect the bound target moiety 111 by evanescent sensing via electromagnetic radiation propagating through the waveguide 105. As illustrated in FIG. 1B, the evanescent field can extend relatively far beyond the waveguide 105, therefore the photonic device 100 allows for sensing of relatively large species (e.g., blood cells) compared with competing techniques (e.g, SPR).

The photonic device 100 includes the optical waveguide 105 disposed on a substrate 107. The device 100 is configured such that waveguiding will occur in the waveguide 105 at desired wavelengths of electromagnetic radiation. In certain embodiments, the device 100 is surrounded on three sides by the ambient environment (e.g., air) and supported by the substrate 107, as illustrated. However, it will be appreciated that cladding layers can be applied to one or more of the free surfaces of the waveguide 105 not abutting the substrate 107.

Still referring to FIG. 1D, a binding moiety 109 is coupled to the surface of the waveguide 105. The binding moiety 109 can be directly coupled to the surface of the waveguide 105, or can be attached to an intermediate layer. Such an intermediate layer may be an anti-fouling layer, as disclosed in the Exemplary Embodiments below.

The binding moiety 109 can be any moiety known to those of skill in the art that will bind to a desired target moiety 111 contained within the sample flow. Representative binding moieties include synthetic or isolated saccharides (mono-, di-, tri-, tetra-, and oligo-) representative of the blood group antigen system, synthetic or isolated antigenic glycoconjugate (glycopeptide, glycolipid, glycosamino glycan) present on human cells and tissues, synthetic or isolated protein and peptide moieties and antigens present on human erythrocytes and other cells and tissues, lipid species specific to erythrocytes and other cells and tissues; whole or fragmented eukaryotic/prokaryotic/viral components; synthetic or modified biomimetic compounds capable of binding to carbohydrate, protein, glycoconjugate or lipid species; synthetic or isolated saccharides (mono-, di-, tri-, tetra-, and oligo-) antigens or binding moieties; antibodies, nanobodies, fab, aptamers, and other antigen-specific capture species.

Representative binding moieties are configured to bind to: blood cells, antigens, antibodies, pathogens, nucleic acids, and other biologically relevant species. In certain embodiments, the photonic device is used to determine blood type from a sample of blood in contact with the device. In such embodiments, at least one binding moiety is used to bind a target moiety is indicative of blood type. Representative target moieties include moieties similar to those listed above for the binding moieties (e.g., because both direct and indirect typing can be used). Additionally, non-antibody-based capture elements can be used instead of antibodies, as well as any binding or target moieties known to those of skill in the art.

In one embodiment, the target moiety indicative of blood type is attached to a blood cell. This approach is referred to as "direct typing", because the blood cell itself is bound to the photonic device 100 (i.e., sensed by the device) through the binding moiety 109 on the waveguide 105 coupling to the target moiety 111 that is part of the blood cell itself. Blood cells include white blood cells, red blood cells, platelets, microparticles, and portions thereof.

In other embodiments, "indirect typing" is used, wherein, the binding coating is an antigen and wherein the target moiety indicative of blood type is an antibody (e.g., through serology) indicative of immunity to blood or pathogen antigens.

While both direct and indirect typing can be used to determine blood type, these techniques can also be used to determine what blood types the blood is immunized against. Accordingly, indirect typing can be used to detect antigens that are indicative of immunity to aspects of a blood type.

Typically, only one of direct and indirect typing will be used on a single photonic device (i.e., a single resonator). This is because each device is configured to only bind to one specific target moiety. This specific binding scheme provides certainty that any binding event detected by the device will indicate the presence of the single desired target moiety. However, because photonic devices (e.g., ring resonators) can be fabricated to have such small dimensions, a single substrate ("chip" or "die") may contain up to thousands of devices, each capable of having a different binding moiety attached to its sensing surface. Therefore, on a single substrate, both direct and indirect typing may be used.

This parallel approach proves particularly powerful when undertaking the typing of blood, which may require sensing of several target moieties (e.g., blood cells and various antibodies) before the blood type can be determined accurately. Using known techniques, these multiple targets would require multiple test runs. Using the present embodiments, a single blood sample can be typed by contacting it with a single substrate containing a plurality of photonic devices having binding coatings configured such that all of the necessary target moieties will be tested for in the sample. By combining the output of the plurality of devices, the target moieties present in the blood can be determined, which, in turn, allows for determination of blood type.

The analysis of blood using both direct and indirect typing is described further below in Exemplary Embodiment 3.

While the devices disclosed have thus far been described as related to blood typing and blood immunology, it will be appreciated that the devices can also be used to determine the presence of a pathogen in a biological sample, such as blood. As with analysis of blood using the devices, the pathogen can be detected directly or indirectly by functionalizing the device with a binding moiety configured to bind to a target moiety indicative of a pathogen. The target moiety indicative of the pathogen can be one of a pathogen, a pathogen-associated antibody, a pathogen associated nucleic acid, and a pathogen-associated antigen.

Binding Coatings

All binding coatings include the binding moiety, as described above. However, the binding coating may also provide other properties. Of particular interest are coatings that improve the compatibility of the device with the sample. Because biological samples, such as blood, are of particular interest, certain coatings are antifouling, so as to decrease (or eliminate) non-specific binding.

While any antifouling coating can be used, in one embodiment, the binding coating is zwitterionic. Other antifouling coatings include hydrophilic polymer substrates (e.g. poly- and oligoethylene glycol, PEG and OEG), mono-, oligo- and polysaccharide-based non-fouling coatings, and protein-based coatings that prevent subsequent blood protein adsorption.

As disclosed in more detail in the Exemplary Embodiments below, zwitterionic films can be configured to provide antifouling properties and can be engineered to be both thin (so as to allow for evanescent detection beyond the film) and to have appropriate binding moieties on a distal surface so as to capture target moieties.

Representative zwitterionic films useful with the embodiments disclosed herein are disclosed in the following references, each of which is incorporated by reference in its entirety: U.S. Pat. No. 7,879,444; U.S. Application Publication Nos. 20110195104, 20090156460, 20100099160, 20100247614, 20100249267, 20090259015, 20110097277, 20080181861, 20110282005, and 20110105712; and PCT Publication Nos. WO 2009/067562, WO 2008/083390, WO 2009/067566, WO 2009/067565, WO 2008/019381, WO 2011/057225, WO 2007/024393, WO 2011/057224, and WO 2011/057219.

In one embodiment, the binding coating comprises a poly(carboxybetaine). However, it will be appreciated that any zwitterionic material can be used as long as it meets the requirements of the devices disclosed herein.

Figure 9:
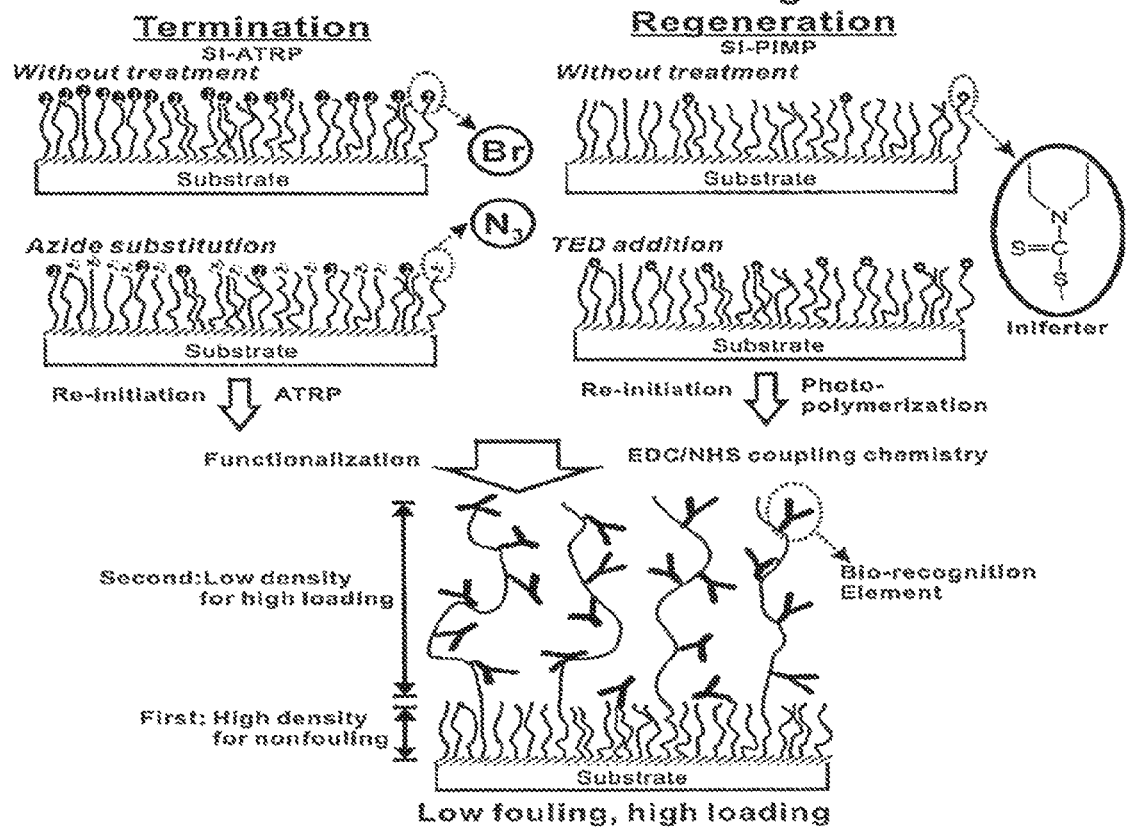
FIG. 9: Illustration of hierarchical platform with an ultra low fouling first layer and high-loading second layer.

In one embodiment, the binding coating comprises a plurality of layers, including an antifouling layer and a capture layer. As disclosed in Exemplary Embodiment 2 (and as illustrated in FIG. 9), the antifouling coating can be engineered to have a plurality of layers, each having a separate function. In one embodiment, the antifouling layer is zwitterionic. In one embodiment, the capture layer comprises at least one binding moiety. In one embodiment, the binding moiety is configured to bind to the target moiety indicative of blood type. In certain embodiments, the binding moiety is an antigen configured to capture circulating antibody to determine indirect type. In another embodiment, the binding moiety is an immobilized antibody or similar antigen-binding moiety to determine direct type.

In one embodiment, the antifouling layer is bound to the capture layer. Multilayer binding coatings are typically covalently or ionically bound together to provide the antifouling functionality and the binding functionality. However, it will be appreciated that any means for combining these functionalities is contemplated. Furthermore, in one embodiment, the binding coating is covalently attached to the sample waveguide. Conversely, in one embodiment, the binding coating is not bound to the sample waveguide.

Photonic Devices

In one embodiment, the sample waveguide is a portion of a photonic device selected from the group consisting of a resonator and an interferometer.

In certain embodiments, the resonators are optical resonators. The optical resonator structures discussed herein can be silicon based nanostructures, and in at least one embodiment include a traveling-wave ring that is coupled to a nearby silicon waveguide. In certain embodiments, the ring resonators have a diameter of 100 microns or less. In other embodiments, the ring resonators have a diameter of 50 microns or less. In at least some embodiments the optical resonator structures employed in this technology are nanoscale. In at least some embodiments, optimized slotted waveguides use sub-100 nm features (e.g., a slot dividing the waveguide in half of 100 nm or less) to concentrate optical fields near the surface of the waveguides, to achieve relatively greater sensitivities than can be provided by surface plasmon resonance (SPR) devices. Such slotted ring resonators and waveguide structures are known in the art.

It should be understood that while a silicon ring resonator structure is an exemplary optical cavity resonator structure that can be used as a photonic device in accordance with the embodiments disclosed herein, the concepts disclosed herein are not intended to be limited to silicon structures or ring resonator structures. The embodiments disclosed herein can be implemented on any photonic devices that can be used for evanescent wave sensing. Furthermore, such photonic can be implemented on varied substrates (not just silicon, as noted immediately above). Thus, where reference is specifically made to silicon ring resonators herein, it should be understood that such a structure is an exemplary and non-limiting embodiment.

Silicon photonics has the potential to revolutionize label-free real-time biosensing. Of particular interest in the present disclosure is the identification of blood type from a sample of whole blood. Through chemistries that can selectively functionalize both oxidized silicon and silicon nitride with moieties capable of selectively binding with targets (such as proteins, bacteria, and other bio-molecules), it is possible to achieve both specificity and extraordinary sensitivity in a chip-scale system based on the use of nano-photonic waveguides. The concepts disclosed herein are based on using the silicon ring resonator, which includes a traveling-wave ring that is coupled to a nearby silicon waveguide. The ring resonator structure's response is a function of the refractive index (i.e., dielectric constant) above the resonator, permitting it to sensitively and specifically detect bound species (e.g., blood cells, antigens, etc.) at or near the surface of the device. Preliminary studies indicate that such ring resonator structures possess sensitivities that exceed that of SPRs, with limits of detection low enough to detect individual small-molecule binding events.

One significance of the use of silicon nano-photonic based devices is that such silicon-based biosensors can be mass-produced with standard silicon fabrication techniques widely employed in the electronics industry, providing economies of scale enabling powerful yet inexpensive sensing devices to be achieved. As compared to SPR devices, a ring resonator device offers much greater sensitivity, potentially at lower cost, with the possibility of truly integrated data acquisition and processing offered by leveraging integrated chip technologies. By integrating optical and electronic complexity (photonic waveguides and transistors) with these sensors, it will become possible to perform thousands of different tests, in real-time, on a single sample, with a chip that could cost a fraction of the cost of traditional biosensors in large volumes. Such a chip would have enormous impact in areas as disparate as disease diagnosis, global health, biological and chemical warfare, homeland security, home health care and diagnosis, and environmental monitoring.

In certain embodiments, a single chip device is provided with photonic structures, switches, detectors, and calibration structures integrated directly onto a single die.

Silicon-on-insulator waveguides provide a remarkable platform for manipulating light on a nano-scale. Because silicon-on-insulator is a standard material for manufacturing nano-scale electronic circuits, it is possible to commercially obtain material of extremely high and consistent quality, and to leverage billions of dollars of commercial nanofabrication infrastructure to build nano-scale devices. This commercial infrastructure also makes silicon an ideal platform for moving rapidly from individual devices into large-scale integrated systems. Silicon is optically transparent at telecommunications wavelengths (near 1.5 μm), making the silicon waveguide a system that is inherently compatible with today's existing fiber optic infrastructure. Lastly, silicon has one of the highest refractive indices of any common dielectric material, allowing silicon waveguides to concentrate light to a remarkable degree, in particular near the surfaces of the waveguides, where the field can interact very strongly with surface bound ligands as well as their targets; viruses, nucleic acids, proteins, and cells.

For evanescent wave sensing, it is extremely desirable to have very large optical fields concentrated near the surface of the optical waveguides, where binding events can occur. By concentrating an optical mode into a very small volume, it is a natural corollary that the peak electric field strength of the optical mode will increase. It is possible, with integrated optics in a high index contrast system like silicon ridge waveguides, to achieve mode field concentrations that are 10,000× or more what is typically achieved for a propagating (non-focused) beam of light in air. In fact, the electric field strength of the optical mode propagating in a typical nano-scale silicon waveguide is comparable to the concentrations that can be achieved at the focus of a tightly converging beam in free space. With a silicon guide, this mode can propagate for centimeters without substantial losses, whereas the focus of a lens is only microns in length. In comparing the sensitivity of a silicon photonic system to a conventional SPR biosensor solution, it is worth considering the relevant path lengths along which light can interact with the ligand molecules. In an SPR system, the light bounces through the thin (~10 nm) layer of ligand only twice. By contrast, with ring resonators, the light will travel around an approximately 50 μm diameter ring many thousands of times on average (or more), providing a radically increased interaction length.

An additional advantage comes from the ability to fabricate many optical devices within the same chip, and to use lithography to align them together. As a result, there is only one alignment needed in packaging the devices; it is possible to address an entire optical system with a single fiber array connecting to the outside world. By integrating multiple devices onto the same chip, a single optical alignment can be used to address hundreds or even thousands of different optical components, all of which can comprise a single complex system.

Such a system could include on-chip resonators, detectors, a switch matrix, couplers, and transistor-based control electronics. This means that once a system is in place to test and package these integrated devices, the marginal cost of adding more complexity to a given device is very small.

One of the great benefits of working in the silicon-on-insulator system for photonics comes from access to cutting-edge lithographic processes. By etching an extremely narrow trench (5-100 nm) down the center of a waveguide, it becomes possible to confine a significant fraction of the propagating optical mode in the low-index slot formed in the center of the guide. The divergence condition for a transverse electric mode, moreover, causes the optical field to be concentrated in the low-index region between the slots.

In certain embodiments, the silicon based ring resonator structure and fluidics components are implemented on an integrated silicon chip. A controller can be implemented as a custom designed circuit (such as an application specific integrated circuit) or a microprocessor and memory, the memory including machine instructions which when executed implement a plurality of functions, including introducing a sample into the ring resonator structure, collecting optical data related to the resonance of the ring structure, and analyzing the results to determine if a particular target moiety has been bound to the ring resonator structure.

In certain embodiments, fluidics components are designed to establish specific conditions in the sampling volume of the ring resonator structure to facilitate the study of the sample volume. The sample may be introduced to one or more devices using fluidics. In such an embodiment, the fluidics components include a configurable micro-fluidic flow cell in which flow can be precisely controlled. Such fluidic components include flow cells that can be incorporated into a silicon based chip. Incorporating micro-fluidics with the photonic devices enable simplified sample delivery, routing, and analysis as related to the photonic devices.

There are many different resonator structures that can be implemented on silicon or silicon related substrates, which can achieve evanescent wave coupling effects at significantly greater distances from a sensor surface than can SPR devices. Such resonator structures, one of which is the silicone ring resonator structure discussed above, include photonic resonator crystals, photonic resonator rings, photonic resonator disks, photonic resonator linear cavities, photonic resonator racetracks, photonic distributed Brag reflectors, and Fabry-Pérot structures. Such structures are encompassed by the term optical micro cavity resonators (or optical cavity resonators). These high-index-contrast optical cavity resonators can be implemented using silicon, silicon nitride, germanium, or any mixture thereof, in crystalline, polycrystalline and amorphous forms.

In another aspect, a photonic system for determining a blood type is provided. In one embodiment, the system includes:

(1) a first photonic device for determining the blood type, comprising:

a first sample waveguide having a first sample surface; and a first binding coating covering and being in optical communication with at least a portion of the first sample surface, the first binding coating being configured to directly bind to a blood cell moiety indicative of the blood type, wherein the blood cell moiety is attached to a blood cell body selected from the group consisting of a blood cell, a blood cell membrane, a blood cell fragment, a microvesicle, and a blood cell-associated antigen, and wherein the first photonic device is configured such that light passed through the first sample waveguide has an evanescent field that extends a distance beyond the first sample waveguide sufficient to detect the bound blood cell moiety; and (2) a second photonic device for determining blood type, comprising:

a second sample waveguide having a second sample surface; and a second binding coating covering and being in optical communication with at least a portion of the second sample surface, the second binding coating being configured to bind to an antibody indicative of the blood type, wherein the second photonic device is configured such that light passed through the second sample waveguide has an evanescent field that extends a distance beyond the second sample waveguide sufficient to detect the antibody indicative of the blood type.

In one embodiment, the first photonic device and the second photonic device are configured to simultaneously determine the blood type. By using simultaneous detection, the output of multiple devices can be compared to determine blood type (or detect a pathogen) in real time.

In one embodiment, the photonic system further comprises a computer configured to determine the blood type using output from both the first photonic device and the second photonic device. By comparing the response of the two different devices having two different binding coatings, a greater depth of information about the sample can be obtained using a single system. For example, both blood type (direct binding) and serology can be performed at the same time on the same sample.

In one embodiment, the photonic system further comprises a reference waveguide that does not have any binding coating. The reference waveguide may be an untreated waveguide that serves as a temperature reference that allows for calibration of the obtained data with regard to the temperature of the devices (e.g., resonators change characteristics with changing temperature and so fluctuations in temperature should be accounted for in interpreting data from devices).

In one embodiment, the photonic system further comprises a third photonic device configured to bind a moiety indicative of a pathogen. Using yet another device, a single sample can also be tested for a pathogen in order to not only characterize the blood, but also pathogens contained therein. In one embodiment, the moiety indicative of a pathogen is selected from the group consisting of a pathogen, a pathogen-associated antibody, a pathogen-associated nucleic acid, and a pathogen-associated antigen.

In additional aspects, methods for testing a biological fluid (e.g., blood) are provided. In the methods, the devices and systems provided herein are exposed to the fluid sample and the effect of the sample on the device characteristics (e.g., resonant wavelength of a ring resonator) in response to binding events on the sample surface of the device are measured. Multiple devices can be used to compare the results of multiple different binding surfaces spread across multiple devices. The testing can be simultaneous across a plurality of devices in order to facilitate real-time testing. Microfluidics can be used to deliver the sample to the devices, as well as buffer and wash treatments. Automation can be accomplished by coordinating (e.g, by computer) the delivery of sample to the device(s) and the measurement of the output of the device(s).

Exemplary Embodiment 1

Photonic Sensing in Undiluted Human Plasma

In the present study, we incorporated a novel self-adsorbing zwitterionic polymer, which is engineered to readily modify the native oxide of silicon-based devices for enhanced performance in complex biological fluids. These zwitterionic polymers, composed of carboxybetaine methacrylate (CBMA) monomers, are charge dense, yet net-neutral. This material property electrostatically induces surface hydration as opposed to hydration by hydrogen bonding interactions, resulting in ultra-low protein fouling when exposed to human plasma and serum.

As demonstrated by the authors, the chemistry described herein has previously enabled the detection of biomolecules at clinically relevant sensitivities in complex media using plasmonic and mechanical sensors. Translating these zwitterionic chemistries to the microring resonator opens the possibility of performing sensitive clinical assays on silicon photonics. Using this approach, we report the label-free detection of a protein at 10 ng ml$^{-1}$ in undiluted human serum, a first in the field of silicon photonics-based biosensing.

For this study, we utilized a microring resonator chip consisting of a number of individual microring sensors. The microrings are rapidly interrogated by an external laser with a center frequency of 1560 nm (approximately 250 ms per microring). Real-time peak-fitting software determines the shift in resonance wavelength of the optical cavity as a function of time. The biosensor chip is coated in a fluoropolymer cladding to minimize waveguide losses. Portions of the cladding have been removed to expose the silicon oxide surface of the microring resonators for chemical modification and subsequent biosensing experimentation. The remaining fluoropolymer-clad microring resonators serve as temperature and vibration reference controls (FIG. 1C). Mylar microfluidic gaskets are used to orthogonally address sets of microring resonators to perform chemical modifications and interrogate biological interactions at the sensor surface. The geometry of the waveguide is a 500×200 nm ridge, as shown in FIG. 1B, while the ring radius is 15 μm.

Figure 2:
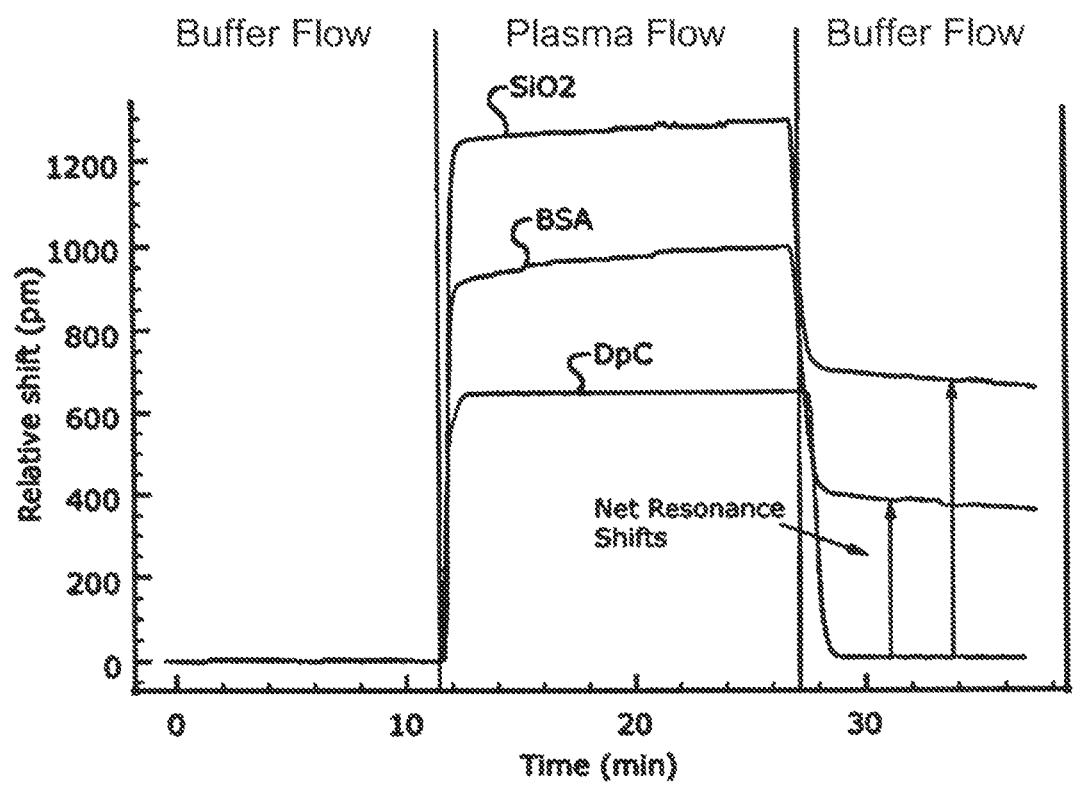
FIG. 2. Relative resonance shift for three microrings with varying surface chemistries during exposure to undiluted human plasma. As illustrated, microrings were subjected to buffer, then human plasma, and returned to buffer. The net resonance shift at the 30 minute mark and beyond is proportional to the amount of adsorbed material on the surface of the microring.

We introduced a self-adsorbing zwitterionic polymer DOPA-pCBMA (DpC) that dramatically reduces non-specific binding to the surface of the silicon microring. Initially, we evaluated the ability of the DpC strategy to prevent non-specific adsorption of protein to the oxide surface on the silicon microring resonator. Microring resonator biosensors were exposed to solutions of DpC or bovine serum albumin (BSA) for surface passivation. The DpC coating was characterized by X-ray photoelectron spectroscopy (XPS) and ellipsometry. To assess the ability of the biosensor surface coatings to resist non-specific protein adsorption, we exposed DpC-modified resonators to solutions of fibrinogen (FIG. 5) and undiluted human blood plasma (FIG. 2). FIG. 2 illustrates relative resonance shift for three microrings with varying surface chemistries during exposure to undiluted human plasma. As illustrated, microrings were subjected to buffer, then human plasma, and returned to buffer. The net resonance shift at the 30 minute mark and beyond is proportional to the amount of adsorbed material on the surface of the microring.

The net shift in resonance wavelength after exposure to human plasma was used to assess the amount of 'fouling' protein adsorbed to the microring resonator surface. While BSA passivation of the sensor surface decreased the amount of 'fouling' protein by around 50% compared to the 660 pm shift seen on bare silicon oxide, the DpC coating resulted in only 5 pm of shift due to fouling in undiluted human plasma. This result demonstrates the noteworthy capability of DpC coatings to yield ultra-low fouling surfaces on silicon photonic devices.

Figure 3A:
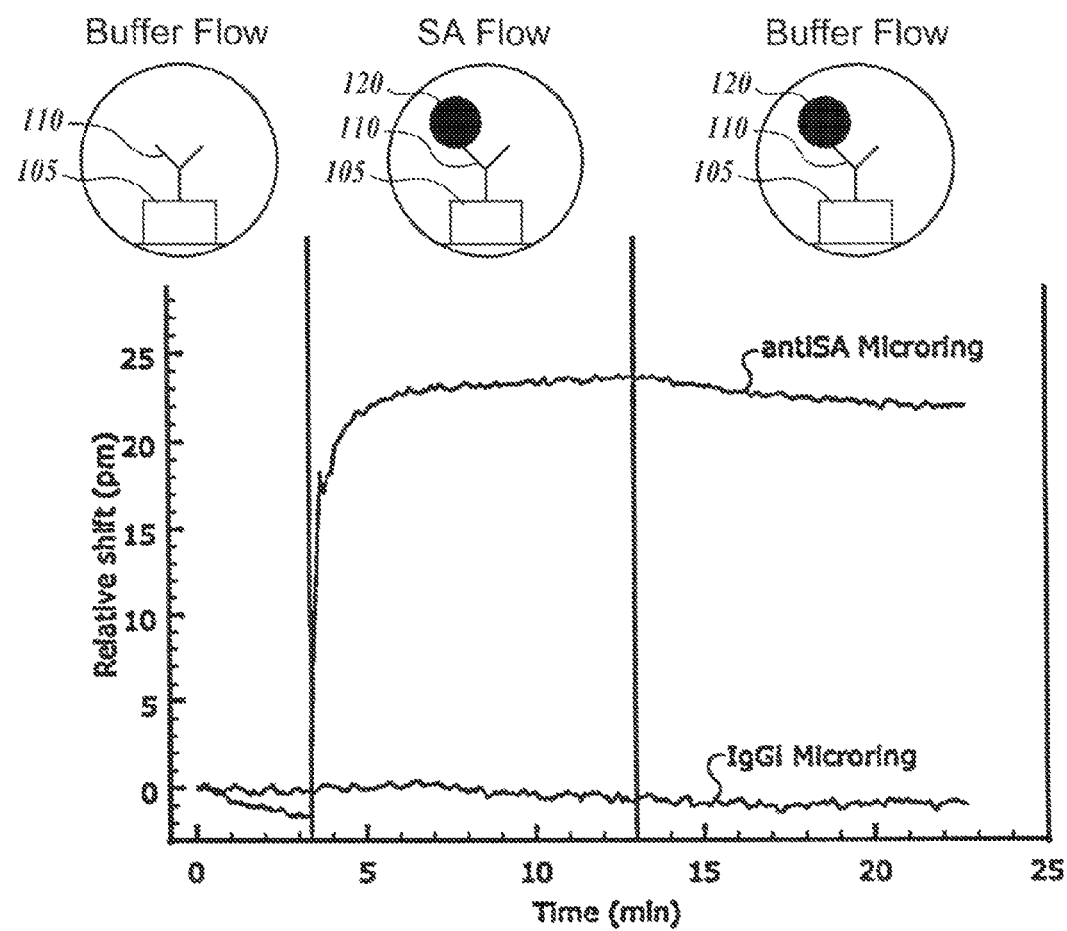
FIGS. 3A-3C. 3A: Resonance peak shifts as a function of time are shown for representative antiSA-DpC and IgGi-DpC microrings. As illustrated, sensors are initially exposed to buffer (PBS), then SA-spiked buffer (20 µg ml$^{-1}$), and returned to buffer. The insets illustrate the process of protein capture on the surface of the antiSA-DpC microring. 3B: Shifts in resonance as a function of increasing concentrations of SA in buffer. 3C: The relative shift difference and a best-fit Langmuir binding curve for the antiSA-DpC and IgGi-DpC microrings as a function of SA concentration.
Figure 6:
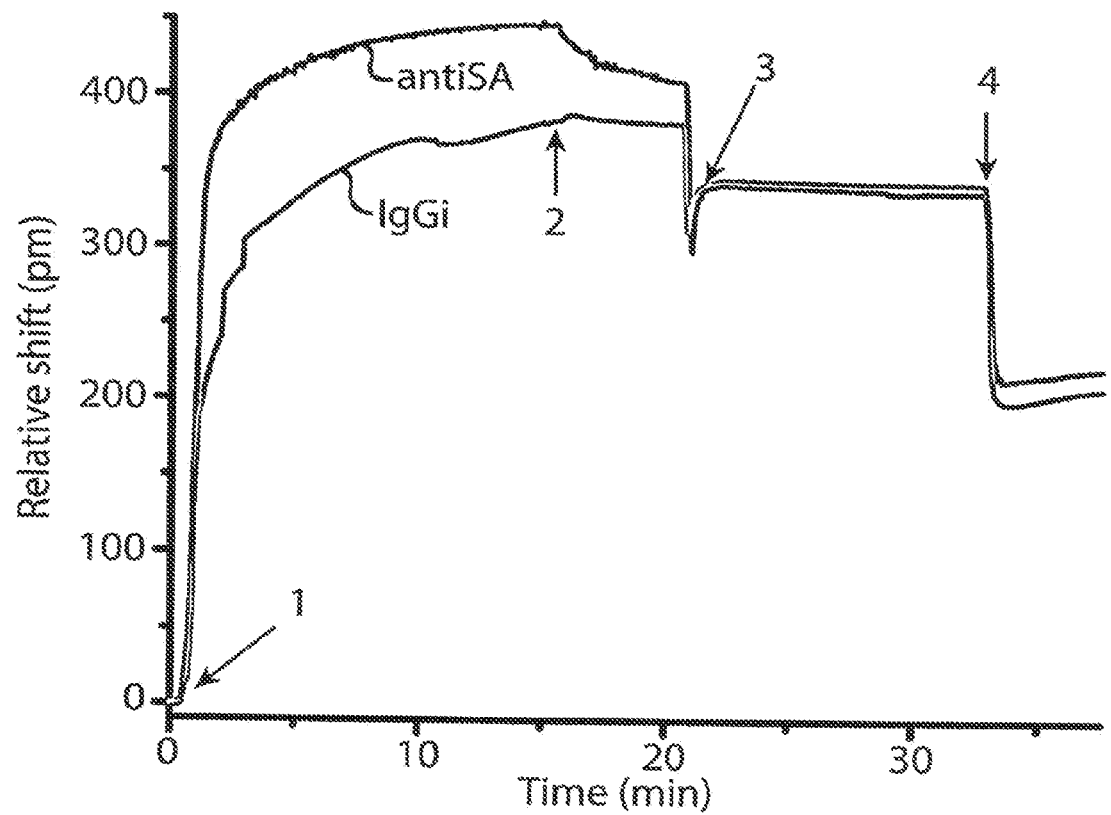
FIG. 6: Representative sensor output for antiSA and IgGi immobilization to DpC-modified microring resonators. After polymer activation (not shown), sensor baseline is achieved in immobilization buffer followed by (1) solutions of antiSA and IgGi for approximately 15 minutes, prior to a brief wash with (2) immobilization buffer. Residual, unreacted DpC chains are deactivated in (3) a high pH buffer. Microrings are exposed to (4) immobilization buffer for overall quantification of immobilized antibody.

In addition to effectively eliminating sensor response to biological noise, the DpC strategy enables facile conjugation of capture ligands that can impart biological function to individual silicon microrings. When exposed to a sample solution, these capture element ligands bind target molecules generating a shift in microring resonance proportional to the target analyte concentration. We employed carbodiimide chemistries to immobilize a monoclonal antibody (antiSA) specific for the model protein analyte, streptavidin (SA). An isotype antibody (IgGi), sharing the same structure as antiSA, but with no binding specificity for SA, was immobilized to adjacent microring resonators to serve as a negative control during subsequent analyses (FIG. 6). To demonstrate specific protein detection, phosphate-buffered saline (PBS) spiked with 20 µg/ml SA was flowed over the microrings, shown in FIG. 3A. In FIG. 3A, the waveguide 105 and antiSA binding moiety 110 are used to capture SA 120. As expected, the antiSA-DpC microrings exhibited specific binding of SA, while control IgGi-DpC microrings had no significant sensor response.

Figure 3B:
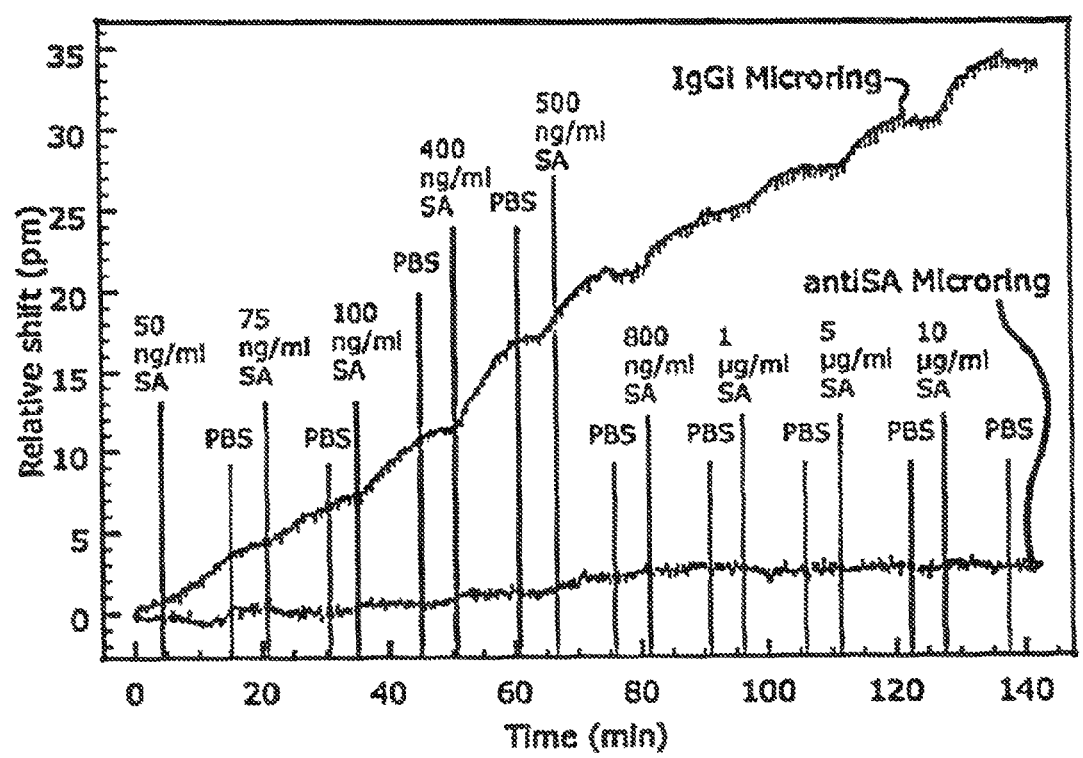

Further experiments were performed to explore the relationship of SA concentration in PBS to the microring resonance shift. AntiSA-DpC and IgGi-DpC microrings were exposed to successively increasing SA-spiked PBS solutions, with intervening unspiked PBS washes, detailed in FIG. 3B. The binding process of SA to antiSA-DpC is known to follow Langmuir statistics and the relative resonance shift difference as a function of target analyte concentration can then be expressed as:

$$d\lambda = A\alpha P/(1+\alpha P) \quad (1)$$

Figure 3C:
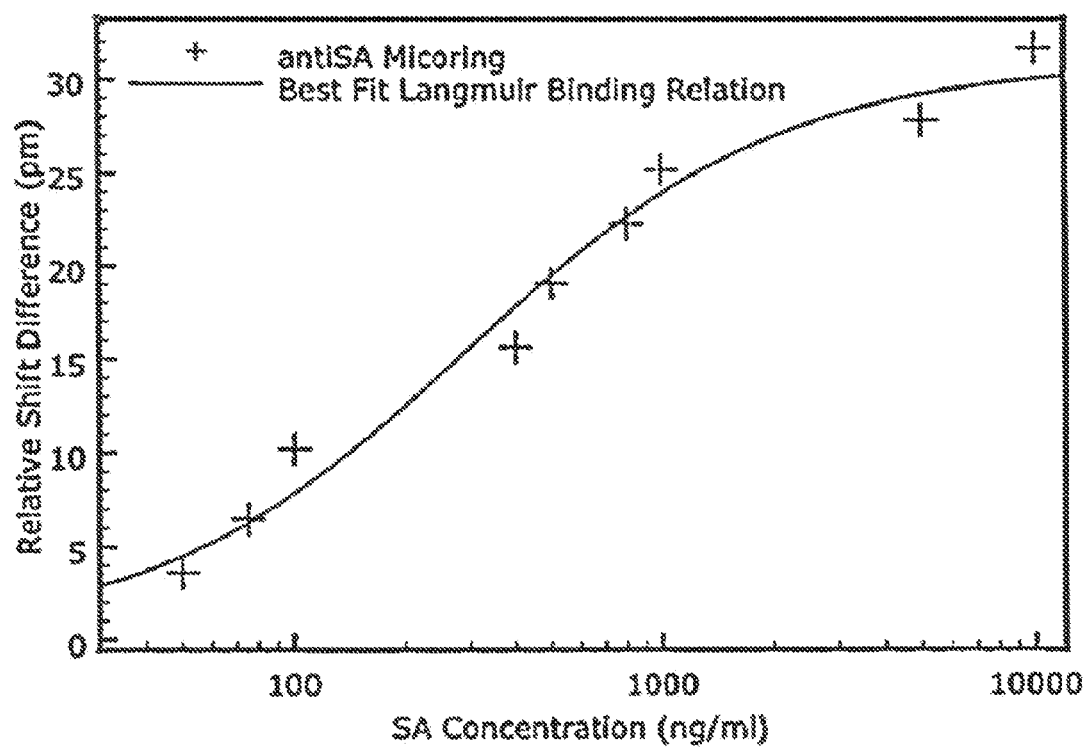
Figure 4A:
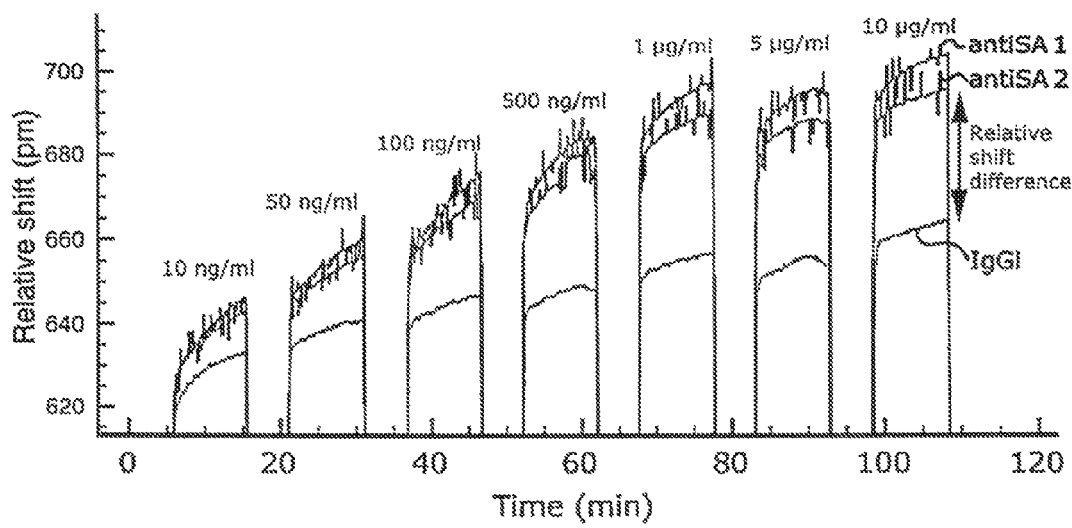
FIGS. 4A and 4B. 4B: The resonance shift as a function of time during exposure to undiluted human serum spiked with increasing concentrations of SA. The microrings are washed briefly with buffer (PBS) between spiked serum samples. The large shift in all microrings when exposed to serum is expected due to the change in refractive index with respect to buffer. The relative shift difference is due to the specific binding of SA to antiSA-DpC sensors. 4A: A detail of the peaks of FIG. 4B.
Figure 4B:
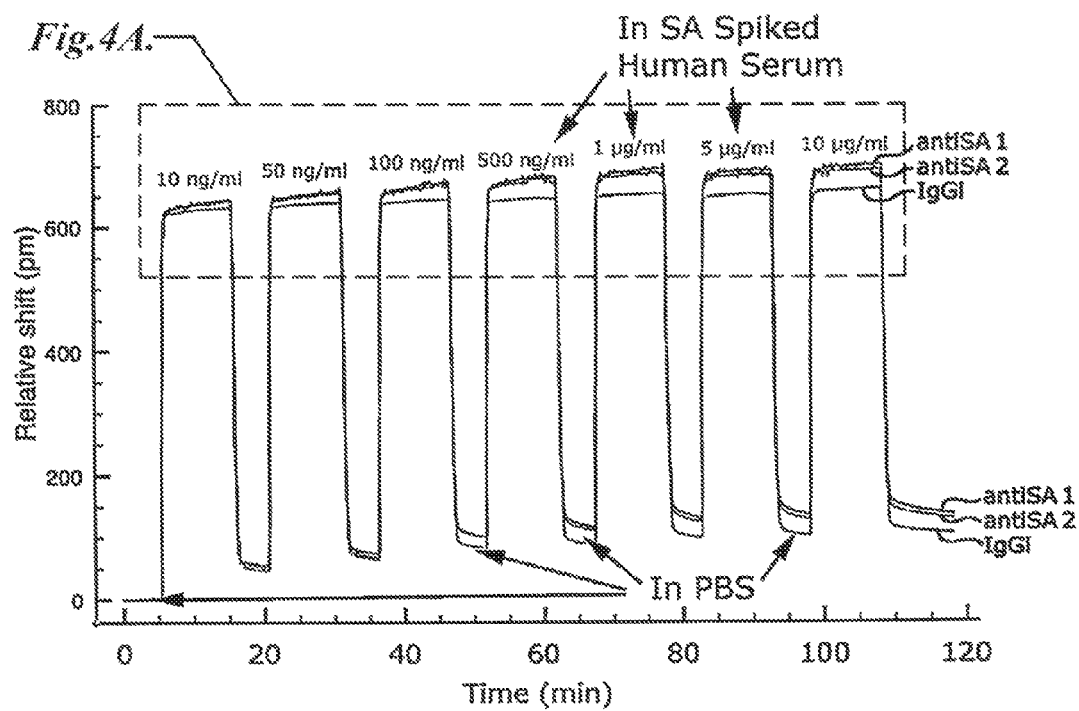

Here, P is the concentration of SA in solution, $\alpha$ is the binding coefficient, A is a constant of proportionality depending on the number of antiSA sites, and the amount of resonance shift per SA molecule, and finally $d\lambda$ is the relative resonance shift difference. A least-squares fit of (1) to the peak shift differences between the antiSA-DpC and IgGi-DpC microrings seen in this experiment is shown in FIG. 3C. Langmuir statistics are followed, with a best-fit binding coefficient $\alpha$ of 0.0034 (ng ml$^{-1}$)$^{-1}$. The primary goal of this study was to demonstrate the detection of analyte in undiluted serum. Undiluted human serum was spiked with SA at concentrations ranging from 10 ng ml$^{-1}$ to 10 µg ml$^{-1}$, encompassing a range of concentrations relevant to clinical diagnostics. Sensors were exposed to increasing concentrations of SA-spiked human blood serum, with PBS buffer washes between samples, as seen in FIGS. 4A (detail) and 4B (full scan).

Figure 7A:
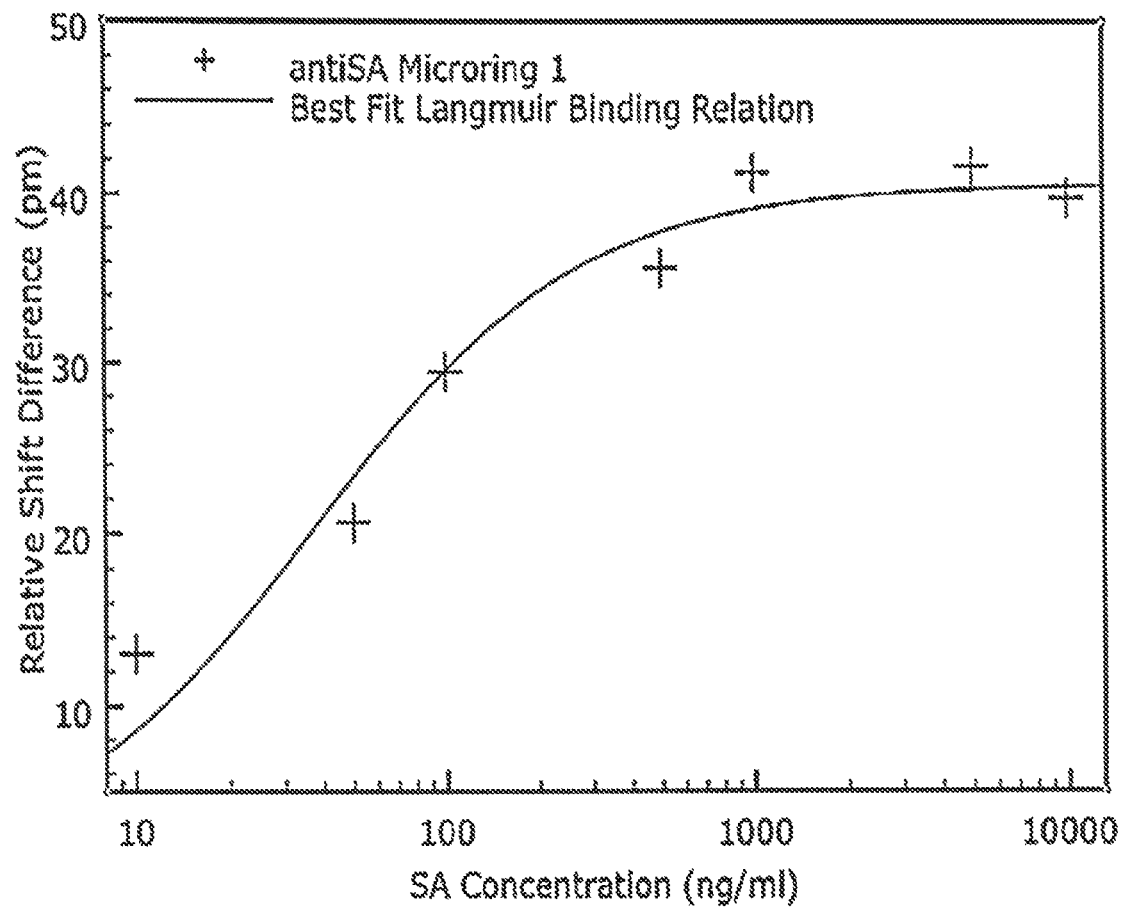
FIGS. 7A and 7B: The relative shift difference of the microrings as a function of SA concentration in human serum for antiSA-DpC Microrings 1 (FIG. 7A) and 2 (FIG. 7B) follow Langmuir statistics, as expected. A best fit Langmuir binding relation is included, yielding binding association constants of 0.027 (ng ml$^{-1}$)$^{-1}$ and 0.026 (ng ml$^{-1}$)$^{-1}$ for Microring 1 and Microring 2, respectively.
Figure 7B:
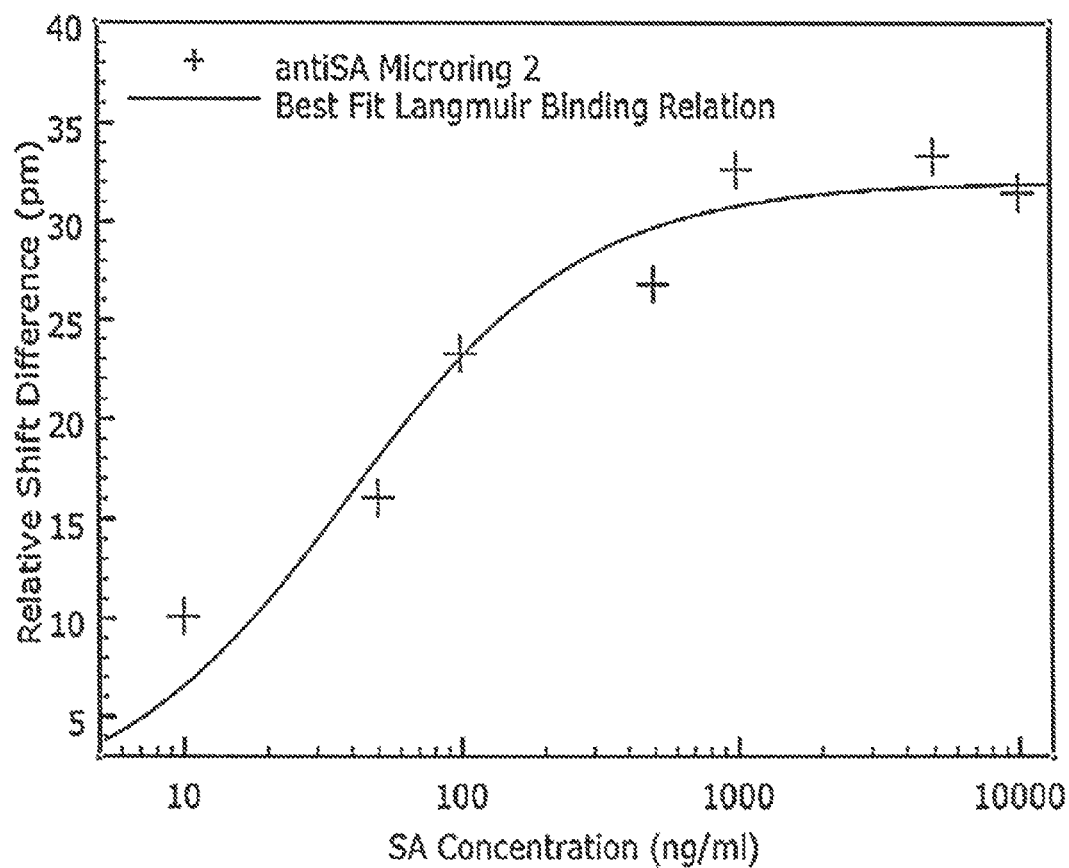

The results of several functionalized microring biosensors are shown. Large resonance shifts are seen on all rings, on the order of 650 pm, due to the difference in average refractive index between PBS and human serum. A clear relative shift difference is seen between the antiSA-DpC microrings and the IgGi-DpC control microring, indicating that SA is being successfully detected. Some increase in the level of fouling is observed when compared to the unfunctionalized DpC coated microrings shown in FIG. 2. This increase is due, in large part, to nonspecific binding of serum proteins to the immobilized antibody capture ligands. Plotting the relative peak-shift differences for the antiSA-DpC and IgGi-DpC microrings, one recovers a relationship that follows Langmuir statistics (FIGS. 7A and 7B). A least squares regression assuming relation (1) yields a binding coefficient of 0.027 (ng ml$^{-1}$)$^{-1}$ and 0.026 (ng ml$^{-1}$)$^{-1}$ for microrings 1 and 2, respectively, with the estimated number of binding sites 5.1×10$^5$ and 3.8×10$^5$. The difference in binding sites between microrings is to be expected, as it is not possible to precisely control the number of antibodies immobilized to the DpC scaffold on each device. Based on the approximate dimensions of the SA molecule (5×5×5 nm$^3$), the observed response at saturation corresponds to 15% surface coverage of the microring in the case of antiSA-DpC Microring 1. It is worth noting that we observe a difference in the binding coefficients when characterizing antiSA-DpC/SA association in buffer versus undiluted serum. This difference in binding coefficients was anticipated due to the differences in solution composition (serum vs. buffer), and the results are comparable to what has been observed in similar biosensing experiments.

Figure 8:
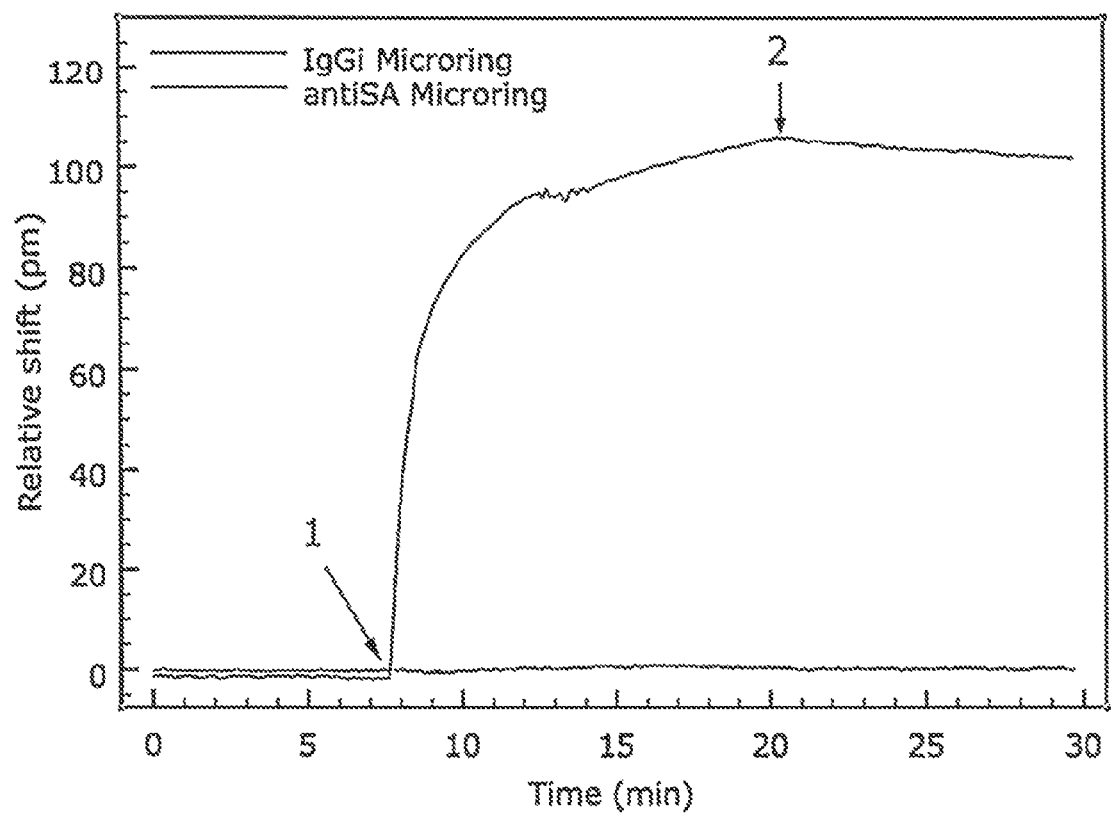
FIG. 8: Response of antiSA-DpC Microring 2 and IgGi-DpC microrings to a second antiSA solution. After the undiluted human serum/PBS exposure steps, the microrings are exposed to (1) a solution of a second antiSA for signal amplification. Microrings are returned to (2) PBS buffer to observe bound antiSA. As expected, IgGi-DpC cannot bind the second antiSA probe, confirming that these devices did not bind SA.

The intrinsic noise of the measurements can be estimated by the squared error between the fitted curve and the data, and is 2.8 pm and 2.5 pm RMS. Assuming a noise floor of 3$\sigma$, the functional biosensors exhibit sensitivities of approximately 10 ng ml$^{-1}$ of SA in undiluted human serum. The achieved limit of detection is an order of magnitude more sensitive than the basic commercial colorimetric ELISA used for protein detection in clinical assays. A further control experiment utilized a second polyclonal antiSA antibody to confirm the specific capture of SA by the antiSA-DpC microrings and the absence of SA on the IgGi-DpC microring (FIG. 8).

To leverage the high sensitivity of silicon photonic-based sensing platforms, robust chemical surface modification is imperative for label-free device performance in complex biological samples. For the first time, we have shown that label-free silicon photonic biosensors can provide ELISA-like sensitivity with extraordinary selectivity in undiluted human serum. This study highlights a rapid, simple, and versatile chemical surface modification for silicon photonic biosensors: coatings of DpC can be deposited on sensors in minutes and can be used to immobilize surface capture elements for biophotonic applications. This development in biocompatible silicon photonics represents a significant step for the application of these devices in clinical diagnostics and the biomedical sciences.

Experimental Methods

Microring Resonator Biosensing Platform

Silicon microring resonator biosensors and corresponding analysis instrumentation were manufactured by Genalyte, Inc. (San Diego, Calif.). Each biosensor chip (6×6 mm) consists of an array of 32 individually addressable microring resonators (30 µm in diameter) suitable for real-time biosensing analysis. Twenty four of these microring resonators are exposed for biosensing and eight are coated with a fluoropolymer-cladding to serve exclusively as temperature and vibration reference controls. Exposed microring resonators can be surface modified using chemistries that are compatible with the native oxide of the silicon waveguides. To minimize waveguide losses, the entire chip is coated with cladding with the exception of the exposed microring sensors, limiting all interactions with a biological sample to designated resonators. An external cavity diode laser with a center frequency of 1560 nm rapidly interrogates grating couplers of individual microring resonators (approx. 250 ms per ring), measuring the shift in resonance wavelength of the optical cavity as a function of time.

Materials

All chemical reagents were purchased from Sigma-Aldrich, Corp (St. Louis, Mo.) and used without further purification unless otherwise noted. Fraction V bovine serum albumin was purchased from EMD Chemicals (Gibbstown, N.J.). Fibrinogen (Fb; Fraction I, bovine plasma) was purchased from Sigma-Aldrich. Human plasma and serum samples were provided by the Puget Sound Blood Center (Seattle, Wash.). Murine monoclonal antibodies against streptavidin and monoclonal immunoglobulin (IgG1) control antibodies were purchased from Abcam, Inc (San Francisco, Calif.). Streptavidin and polycloncal anti-streptavidin antibodies (for secondary antibody probe experiments) were purchased from Vector Laboratories (Burlingame, Calif.). All buffers used for biosensing experiments were prepared using ultrapure deionized water (Barnstead Nanopure; Dubuque, Iowa). The pH of buffer solutions was adjusted using 1M solutions of sodium hydroxide (NaOH) or hydrochloric acid (HCl). Phosphate-buffered saline (PBS, pH 7.4) was composed of 10 mM phosphate (1.9 mM $KH_2PO_4$, 8.1 mM $Na_2HPO_4$) and 150 mM sodium chloride (NaCl). Polymer deposition was performed in deposition buffer (10 mM tris(hydroxymethyl)aminomethane (Tris), pH 8.5). Surface grafted polymer coatings were activated using freshly prepared solutions of 0.4M 1-Ethyl-3-[3-dimethylaminopropyl] carbodiimide hydrochloride (EDC) and 0.1M N-hydroxysuccinimide (NHS) purchased from Sigma-Aldrich. Antibody immobilization buffer was composed of 10 mM HEPES (4-(2-hydroxyethyl)-1-piperazineethanesulfonic acid) at pH 7.8. Silicon wafers used for XPS characterization and ellipsometry measurements were purchased from Silicon Valley Microelectronics (San Jose, Calif.). Hydrogen peroxide ($H_2O_2$) and sulfuric acid ($H_2SO_4$) solutions were purchased from J.T. Baker (Phillipsburg, N.J.) and Sigma-Aldrich, respectively. Ethanol was purchased from Deacon Laboratories (King of Prussia, Pa.).

Synthesis of DOPA-pCBMA (DpC) Conjugates

The synthesis of DpC polymer conjugates has been described in detail in previous publications. Briefly, an initiator molecule was synthesized containing two adhesive catechol groups ($DOPA_2$; N,N'-(2-hydroxypropane-1,3-diyl)bis(3-(3,4-bis(tert-butyldimethylsilyloxy)phenyl)-2-(2-bromo-2-methylpropanamido)propanamide)) as described previously. Following synthesis of the CBMA monomer, DpC was polymerized by atomic transfer radical polymerization (ATRP) methods overnight. DpC conjugates were purified by dialysis, resulting in a white powder. The tert-butyldimethylsilyloxy protecting groups were deprotected using 1M tetrabutylammonium fluoride in tetrahydrofuran (THF). The polymer was washed extensively in THF, dried under reduced pressure, and was aliquoted for storage at −20° C. prior to use.

Polymer Deposition on Silicon Microring Resonator Arrays:

Prior to surface modification with DpC conjugates, microring resonator biosensor chips were vigorously cleaned to remove trace organics. Chips were exposed to freshly prepared piranha solution (1:1 30% $H_2O_2$: 98% $H_2SO_4$) for 10 minutes with mild agitation to remove bubbles that formed on the fluoropolymer-clad chip surface (Caution! Piranha solution is extremely dangerous as it can react explosively in the presence of organics). Biosensor chips were washed with copious amounts of water prior to the deposition of DpC conjugates on the bare oxide surface of silicon microring resonators.

The deposition of DpC on microring resonator arrays was monitored in real-time by analyzing the change in the resonance wavelength of individual microrings over time. All solutions were introduced to sensors at a flow rate of 20 μL/min using two alternating 50 μL, negative-pressure syringe pumps controlled by computer software (Genalyte, Inc). Prior to deposition, deprotected DpC conjugates were diluted to a concentration of 1 mg/ml in deposition buffer (10 mM Tris-HCl; pH 8.5). The DpC solution was sonicated for 20 minutes to ensure they were fully dissolved. The biosensor chip was exposed to deposition buffer to establish a signal baseline prior to introduction of the polymer solution. An array of microring resonators was exposed to the sonicated DpC solution (1 mg/ml) for 15 minutes, resulting in high-density deposition of DpC conjugates on the exposed oxide of the microring sensor surface. Microring resonators were then washed with deposition buffer for 5 minutes, followed by an extensive wash (12 minutes) in phosphate buffered saline (PBS; pH 7.4) to remove loosely bound DpC conjugates. Finally, all sensors were exposed to deposition buffer for the quantification of DpC surface coverage by comparing the net shift in resonance wavelength to the initial sensor baseline determined in deposition buffer. As a control, a second array of microring resonators was exposed to a solution of 1 mg/ml BSA prior to performing protein fouling assays on each microring resonator biosensor chip. BSA surface functionalization was performed in parallel with DpC deposition.

Figure 5:
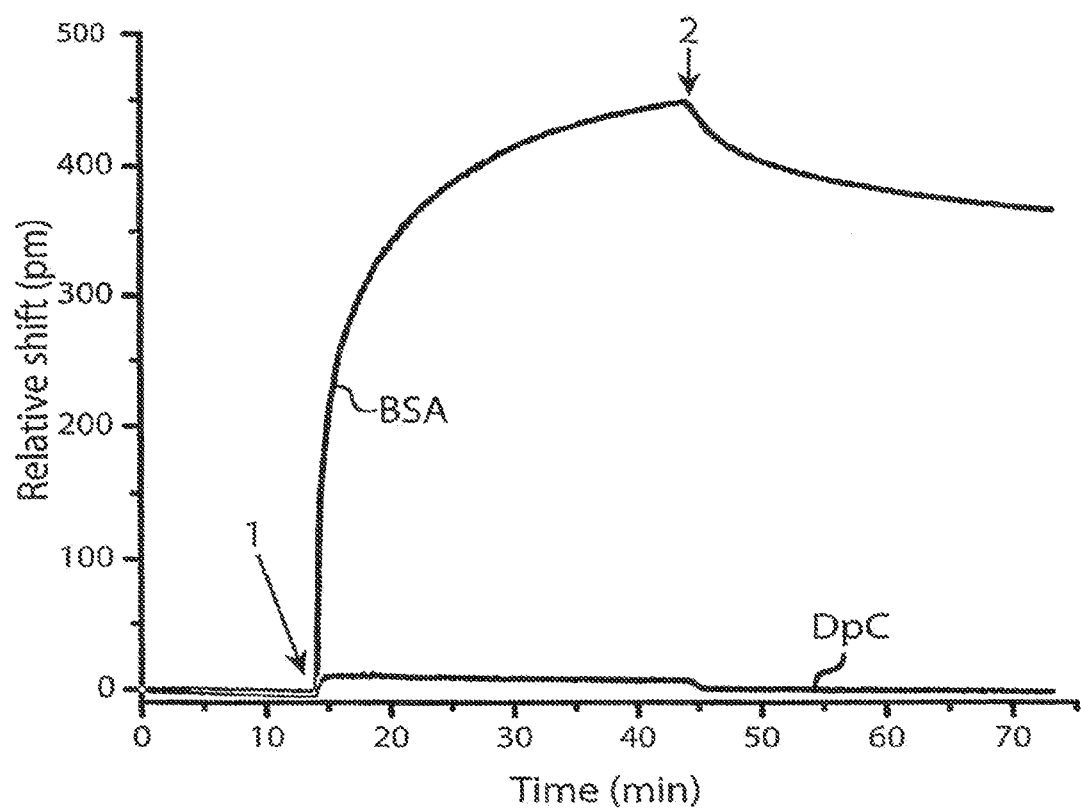
FIG. 5: Protein fouling on sensors exposed to (1) a solution of fibrinogen in PBS (1 mg/ml). Microrings are returned to (2) PBS buffer to observe dissociation of non-specifically adsorbed fibrinogen. BSA-modified microrings are susceptible to fibrinogen fouling, as evidenced by a ~365 pm shift in the net resonance wavelength of the device. However, DpC-modified microrings are highly resistant to fibrinogen adsorption, resulting in no significant overall shift in the resonance wavelength of the microring.

Protein Fouling Assays Using Protein Solutions:

The non-fouling character of DpC-coated and BSA-coated microring resonators was assessed by examining their resistance to protein fouling in simple and complex biological solutions. All solutions were flowed at 20 μL/min and results were monitored in real-time as detailed above. After establishing a baseline in PBS, surface modified (DpC- and BSA-coated) microrings were exposed to 1 mg/ml fibrinogen for 30 minutes, prior to returning to PBS for 30 minutes to assess dissociation of unbound protein (FIG. 5). The overall shift in resonance wavelength was used to compare the amount of protein fouling for DpC- and BSA-coated sensors. The ability of the surface modified sensors to resist protein fouling in complex biological solutions was assessed using undiluted human plasma (FIG. 2). After establishing a baseline in PBS, sensors were exposed to undiluted human plasma for 15 minutes. After returning to PBS, the overall shift in resonance wavelength was used to compare the amount of protein fouling for each surface modification strategy. The results were compared to the amount of protein fouling on unmodified (bare oxide) microring resonators following extended exposure to undiluted human plasma.

X-Ray Photoelectron Spectroscopy (XPS) Characterization of DpC Polymer Film:

Prior to XPS characterization of DpC films, the silicon substrate was cleaned with piranha solution, as detailed above. DpC was deposited on the silicon from a 10 mM Tris-HCl buffer for 20 minutes. The substrate was rinsed vigorously with Tris-HCl buffer, PBS, ultrapure water, then dried under a stream of nitrogen for XPS analysis. XPS composition data (Table 1) were acquired on a Kratos AXIS Ultra DLD instrument equipped with a monochromatic Al—Kα X-ray source (hv=1486.6 eV). XPS data were collected at 0° takeoff angle in the hybrid mode with approximately 10 nm sampling depth, using a pass energy of 80 eV. Three spots on duplicate samples were analyzed. Reported compositional data were averaged over multiple spots. Data analysis was performed on the CasaXPS software (Casa Software Ltd.). As expected, DpC modification of the native oxide of silicon decreases the percent composition of silicon (Si 2p), while increasing the percent composition of organic material (C 1s, N 1s, O 1s) at the substrate surface.

TABLE 1

Relative compositions of bare Si and DpC-modified Si substrates as determined by XPS; n = 3, n/d: chemical species not detected.

|  | Bare Si chip | DpC-modified Si chip |
|---|---|---|
| Si 2p | 45.9 ± 2.8% | 11.1 ± 0.6% |
| C 1s | 19.9 ± 5.3% | 56.1 ± 0.6% |
| O 1s | 34.2 ± 2.5% | 24.4 ± 0.8% |
| N 1s | n/d | 2.3 ± 0.1% |
| Na 1s | n/d | 2.8 ± 0.3% |
| Cl 1s | n/d | 3.2 ± 0.3% |
| Total | 100% | 100% |

Ellipsometry Measurements of DpC Dry Film Thickness:

Prior to dry film thickness characterization, the silicon substrate was exposed to solutions of DpC (1 mg/ml in 10 mM Tris-HCl) or BSA (1 mg/ml in PBS) for 30 minutes. Treated substrates were washed vigorously with their respective buffers, then ultrapure water, and dried under a stream of nitrogen. To determine the dry film thickness of DpC and BSA films on silicon, measurements were obtained using an ellipsometer (M-2000; J. A. Woollam, Inc; Lincoln, Nebr.). The amplitude component ($\Psi$) and phase difference ($\Delta$) were measured for DpC-modified and BSA-coated silicon substrates from 200-1000 nm wavelengths at varying angle of incidence (65°, 70°, 75°) at 9 spots on each chip. The data obtained from measurements was fit using a generalized Cauchy layer ($A_n$=1.45, $B_n$=0.01, $C_n$=0). The thickness of the native oxide layer of the silicon substrates was determined as described above and applied to the Cauchy layer fit (~2.2 nm). The average dry film thickness of DpC and BSA films on the silicon substrates (Table 2) suggest that the polymer surface modification strategy results in very thin coatings capable of strongly resisting protein fouling.

TABLE 2

Ellipsometry characterization of DpC and BSA films on native oxide of Si substrates

|  | Average Thickness (n = 9) | MSE |
|---|---|---|
| BSA film | 3.27 ± 0.25 nm | 3.16 |
| DpC film | 1.08 ± 0.10 nm | 2.83 |

Immobilization of Antibodies to DpC-Modified Microring Resonator Biosensors:

The terminal carboxylate groups of DpC-coated microring resonators were activated using carbodiimide chemistry prior to antibody immobilization. A freshly prepared activation buffer (0.4M EDC, 0.1M NHS) was passed over the DpC-modified sensors twice for 5 minutes, separated by a 1 minute wash steps with ultrapure water. Activated DpC-coatings on microrings were exposed to either monoclonal anti-streptavidin (antiSA) or immunoglobulin control antibodies (IgGi, negative control) as follows. Activated DpC-microrings were briefly exposed to immobilization buffer (10 mM HEPES, pH 7.8) to establish a baseline, followed by immediate exposure to antibody solutions (20 µg/ml in 10 mM HEPES, pH 7.8) for 12 minutes (FIG. 6). After antibody immobilization, the activated-DpC was quenched via hydrolysis at elevated pH (10 mM HEPES, 300 nM NaCl, pH 8.2) for 15 minutes, followed by immobilization buffer to reestablish baseline and determine the amount of immobilized antibody.

Selection Criteria for Functional Microrings for Further Analysis:

Small differences in the level of immobilized antibody, as determined by the overall shift in resonance wavelength, had a significant affect on the performance of functionalized sensors. Therefore, we analyzed microring resonators that responded with 200 pm of overall resonance shift following antibody immobilization for analyte detection in undiluted human serum. We also found that high levels of antibody immobilization (>200 pm in our studies) led to a decrease in the non-fouling nature of the DpC-coating in complex media, resulting in increased non-specific adsorption and a decreased capacity to detect analyte at low concentrations. We found that this quantitative cut-off was not required for detection of analyte in buffer for this proof-of-concept demonstration. This process emphasizes the need to fabricate and analyze arrays of silicon photonic devices in order to assess the uniformity of elaborate surface modifications.

Detection of Streptavidin in Buffer and Undiluted Human Serum:

The model protein streptavidin (SA) was used to demonstrate specific detection of analyte in either buffer or undiluted human serum by antibody functionalized DpC-modified microring resonators. IgGi-DpC modified microrings served as a negative control for non-specific SA binding to immobilized antibodies. To demonstrate analyte detection in buffer, SA was diluted in PBS at concentrations ranging from 50 ng/ml to 10 µg/ml. After establishing a signal baseline in PBS, increasing concentrations of SA in PBS were introduced to microring resonators for 5 minutes. Concentration steps were separated by 5 minute buffer (PBS) washes. The shift in resonance wavelength of antiSA-DpC microrings was compared to IgGi-DpC microrings to demonstrate specific streptavidin detection in buffer.

SA detection in undiluted serum was confirmed by exposing microring resonators to a series of SA-spiked human serum samples. To obtain sensitive device measurements, undiluted SA-spiked human serum samples (10-10,000 ng/ml) were flowed over microrings for 10 minutes per sample (20 µL/min) using a negative-pressure syringe pump (Chemyx, Inc; Stafford, Tex.) equipped with 5 mL glass syringes (Hamilton, Co; Reno, Nev.). Samples were separated by 5 minute buffer (PBS) washes. Specific SA binding was defined as the difference in sensor response between antiSA-DpC and IgGi-DpC microrings. Functionalization of surface grafted-DpC resulted in a small increase in protein fouling compared to unmodified DpC coatings. However, there is little protein accumulation over time. Specifically, antibody functionalized DpC-modified microrings showed ~50 pm of fouling after an initial exposure to serum. However, over 60 minutes of additional exposure to undiluted serum resulted in ~55 pm of additional protein fouling. These results demonstrate that DpC coatings may be functionalized with biomolecules while largely retaining their non-fouling properties during extended exposure to undiluted human serum.

Resonance Shift Calculations:

Consider a cross-section of a waveguide, expressed as $\in(x,y)$ over area $\Omega$. It can be shown that if a portion of the waveguide cross section, $\Omega'$, experiences a shift in dielectric constant $d\in(x,y)$, the shift in effective index (for small changes) will be:

$$dn_{eff} = \frac{\int\int_{\Omega'} |E|^2 d\varepsilon(x,y) dxdy}{2Z_0 \int\int_{\Omega} \text{Re}(E^* \times H) \Box z\, dxdy} \quad (2)$$

For the experiments described in this study, two types of index shifts are relevant. First, an index shift can be created by a bulk change in the refractive index surrounding the waveguide, perhaps from switching the fluid from PBS to human serum. For the 500×200 nm waveguide utilized, if the cladding index is close to 1.35, the index of phosphate-buffered saline (PBS), this shift can be calculated as:

$$dn_{eff} = 0.06 d\in_{clad} \quad (3)$$

Another type of index shift is caused by a molecule becoming bound to the surface of the microring. In this case, the integral in (2) should be taken over the entire area into which the molecule might bind, call this $\Omega'$, and then the result discounted by $A/\Omega'$, where A is the cross-sectional area of the molecule. The molecules under investigation in this work have typical sizes ranging from 5 to 15 nm. The hydrated DpC layer is also estimated to be on the order of 10 nm. Therefore all index shifts occur within 30 nm of the surface of the waveguide. The optical fields exhibit minimal falloff over such a short distance, rendering the index shift independent to small changes in positioning of the molecules. Once the index shift is known, it is easy to calculate the shift in resonance wavelength:

$$d\lambda = \lambda \frac{dn_{eff}}{n_g} \quad (4)$$

Here $n_g$ is the group index of the waveguide, 4.05 near 1550 nm. The waveguide effective index is 2.33. For a molecule, (4) would need to be multiplied by $L'/L$, the length of the molecule, divided by the circumference of the microring, in this case 94 μm. Combining all these expressions, we have:

$$d\lambda = \left(\frac{\lambda}{n_g L}\right) \left(\frac{\frac{1}{\Omega'}\int\int_{\Omega'} |E|^2 dxdy}{2Z_0 \int\int_{\Omega} \text{Re}(E^* \times H) \Box z\, dxdy}\right) \frac{m}{\rho} (\varepsilon_{molecule} - \varepsilon_{background}) \quad (5)$$

Here m is the total mass of bound molecules, $\rho$ is the density of the molecule, and $\in_{molecule}$ and $\in_{background}$ are the dielectric constants of the molecule and background materials, respectively. We have due to numerical calculation:

$$\left(\frac{\frac{1}{\Omega'}\int\int_{\Omega'} |E|^2 dxdy}{2Z_0 \int\int_{\Omega} \text{Re}(E^* \times H) \Box z\, dxdy}\right) = 0.93 \frac{1}{\mu m^2} \quad (6)$$

Also:

$$\left(\frac{\lambda}{n_g L}\right) = 0.0041 \quad (7)$$

We can now calculate the index shift per binding event, or equivalently, the total mass bound, for a molecule where we know the refractive index and density. As noted in the main paper, there is a simple linear relation between the bound mass and the wavelength shift of a resonance peak. Streptavidin (SA) and antiSA should have approximate refractive index 1.45, density 1.35 g/ml, and respective molecular weights of 60, 150 kDa. We note that the approximately 600 pm resonance shift seen in the human serum experiments suggests that the index of human serum is 1.36. The shifts predicted in (4) should then be nearly identical for a given bound molecule, regardless of whether the background is PBS or human serum. We have, finally, $7.86 \times 10^{-5}$ pm of shift per SA binding event in PBS. This can also be expressed as a mass sensitivity; 0.79 pm/fg of resonance shift is expected, in agreement with the 0.89 pm/fg measured elsewhere for a similar system. The number of SA binding sites for a given peak resonance shift difference can then be readily calculated.

Confirmation of Specific Streptavidin Binding to antiSA-DpC Microrings:

To confirm specific SA binding to antiSA-DpC microrings, a polyclonal antiSA antibody (50 μg/ml) was flowed over sensors after detection of SA in serum. By analyzing the formation of an antibody "sandwich" (antiSA/SA/antiSA-DpC), we were able to determine if there was specific capture of SA by the antiSA-DpC sensors. The antiSA-DpC microrings exhibited a significant peak shift, while the IgGi-DpC control microring showed no shift (FIGS. 7A and 7B). This suggests that the bound SA on the antiSA-DpC microring was able to bind the polyclonal antiSA antibodies as expected, while simultaneously confirming a lack of SA bound to the IgGi-DpC microring. The net peak shift, approximately 100 pm, was around a factor of 3 larger than the final relative peak shift of the antiSA and IgGi microrings, which was approximately 30 pm. This is as expected, due to the relative molecular weights of 60 and 150 kDa for SA and antiSA respectively. Further, this result indicates an approximate 1:1 correspondence between the final number of SA molecules bound, and the final number of polyclonal antiSA antibodies bound from solution.

Exemplary Embodiment 2

Hierarchical Anti-Fouling Layer for Photonic Sensing

Surface chemistries for biosensors, implantable medical devices targeted drug/gene delivery carriers, tissue scaffolds, and targeted molecular imaging probes in complex media remain a great challenge due to high nonspecific adsorption and low binding capacity of molecular recognition elements. Currently, few materials have been developed to reduce nonspecific protein adsorption, including poly(ethylene glycol) (PEG), mannitol tetraglyme, and zwitterionic polymers. The effectiveness of protein resistant materials relies on their high surface packing densities. Unfortunately, highly dense two-dimensional (2D) polymer films elicit the limitation of a low ligand-binding capacity. At the same time, a three-dimensional (3D) carboxymethylated dextran-based hydrogel binding matrix was previously developed, enabling very high protein loading due to an open polymer structure.

However, this open structure only provides weak surface resistance to nonspecific protein adsorption, particularly in complex media such as blood. New polymers with precisely controlled architecture are desirable for exploring novel structure-property correlations and achieving unique properties for many applications. In this communication, we propose a unique strategy of developing hierarchical polymer films with structurally regulated functionalities through integrating 2D and 3D structures so as to achieve ultra low nonspecific binding and high loading of molecular recognition elements.

Our first attempt to construct a binding platform with a hierarchical architecture was demonstrated with two distinct surface-initiated techniques. These "grafting from" approaches, based on controlled "living" radical polymerizations, were particularly promising for the preparation of polymer brushes as they permit precise control over chemical composition, film thickness, and architecture. As shown in Scheme 1, the films were prepared via surface initiated atom transfer radical polymerization (SI-ATRP) and surface initiated photoiniferter-mediated polymerization (SI-PIMP). The first layer was grown in a controlled manner to reach a high surface packing density. The second layer, with a low surface packing density, was achieved through "termination" or "regeneration" of the living capped species at the polymer chain end for SI-ATRP and SI-PIMP, respectively.

Due to the dual functionality of poly(carboxybetaine) (pCB) films, a proof-of-concept experiment was performed with zwitterionic pCB using a surface plasmon resonance (SPR) biosensor for demonstrating the novel hierarchical architecture. Previous reports of surface-tethered pCB brushes formed by both SI-ATRP and SI-PIMP have achieved excellent resistance to nonspecific protein adsorption in the presence of complex media, such undiluted human blood serum and plasma, to fouling levels below 5 ng $cm^{-2}$. These fouling levels can be maintained following the immobilization of around 250 ng $cm^{-2}$ of antibody using conventional 1-ethyl-3-(3-dimethylaminopropyl)-carbodiimide and N-hydroxysuccinimide (EDC/NHS) coupling chemistry under biologically friendly conditions. However, this functionalization level only corresponds to an IgG monolayer. Herein, pCB-based platforms with hierarchical structures on a SPR sensor surface are presented for the sensitive quantification of IgG immobilization, antigen binding, and nonspecific protein adsorption.

As shown in FIG. 9, ATRP was combined with a "termination" approach for demonstrating the novel architecture. ATRP involves a dynamic equilibrium between activated propagating radicals and dormant halide end-capped polymer chains, yielding low polydispersity and controlled growth. This "living" characteristic enables re-initiation from macroinitiators for the synthesis of block copolymers. In order to achieve hierarchical pCB films possessing ultra low fouling and high loading properties via SI-ATRP, a densely packed first layer was grown from a gold coated SRP chip modified with an alkyl bromide terminated self-assembled monolayer (SAM). The chips were then submerged in a methanolic solution containing 2,2' bi-pyridine, CuBr, and CB monomer under nitrogen protection and allowed to react overnight. The resulting thickness was 7.6±0.3 nm (Table 3). Importantly, these conditions enabled a highly dense yet thin film to be grown. While the high density is key for achieving low fouling, a thin film is desired for many sensing applications, such as SPR, as the signal intensity/sensitivity decays exponentially from surface of the metal substrate. To establish a hierarchically structured pCB film for increasing the binding capacity, the macroinitiator density for re-growth of the second pCB layer was regulated via azide substitution of bromide species thus "terminating" the future growth of the corresponding chains during the second ATRP reaction. The density of the polymer chains can be controlled by the azide concentration and reaction time. In this study, a 2 hr submersion using an azide concentration of 0.1 M produced the optimal second layer polymer density for protein immobilization. For the growth of the second pCB layer, water-accelerated polymerization with a solvent consisting of 50% water in methanol was employed to induce a high polydispersity of polymer chains. The resulting thickness of the structured film with azide substitution was higher than that without treatment. This is in agreement with previous reports showing rapid bimolecular termination at high initiator densities using aqueous ATRP whereas more dilute initiators enabled continued linear and controlled polymer growth.

TABLE 3

Thickness of films prepared via SI-ATRP and SI-PIMP with and without treatment to capped species.

| | SI-ATRP Thickness (nm) | SI-PIMP Thickness (nm) |
|---|---|---|
| First Layer | 7.6 ± 0.3 | 10.8 ± 0.8 |
| Re-growth (without treatment) | 13.2 ± 0.3 | 32.1 ± 0.6 |
| Re-growth (with treatment) | 17.5 ± 0.9 | 46.1 ± 1.6 |

In contrast to SI-ATRP, SI-PIMP is apt to release capped species from the polymer chains during polymerization, primarily due to bimolecular termination. This irreversible termination significantly hampers future polymer growth. Therefore, in order to control the chain density of the second layer via SI-PIMP, a "regeneration" approach was adopted in which the addition of a deactivator, tetraethylthiuram disulfide (TED), was able to preserve the end-capped photoiniferter groups on the grafted polymers for re-growth of the second layer with controlled grafting density. SPR gold substrates were first modified with the photoiniferter (N,N-(Diethylamino)-dithiocarbamoylbenzyl(trimethyoxy)-thiol (DTCA)) to form SAMs. Similarly to SI-ATRP, the first layer for SI-PIMP was also synthesized in 100% methanol to form a highly dense and thin film. Reactions were conducted using a 30 min UV irradiation and the resulting film thicknesses are shown in Table 3. The first layer thicknesses prepared with 2 μM TED was comparable to that without TED (11.1±0.6 nm). Subsequently, the films were re-initiated in a 90% water/methanol solution resulting in TED treated films with greater thicknesses than those made without, reflecting the ability of TED for preserving the reactive photoiniferter end groups and thereby maintaining the "living" characteristic of SI-PIMP.

Figure 10A:
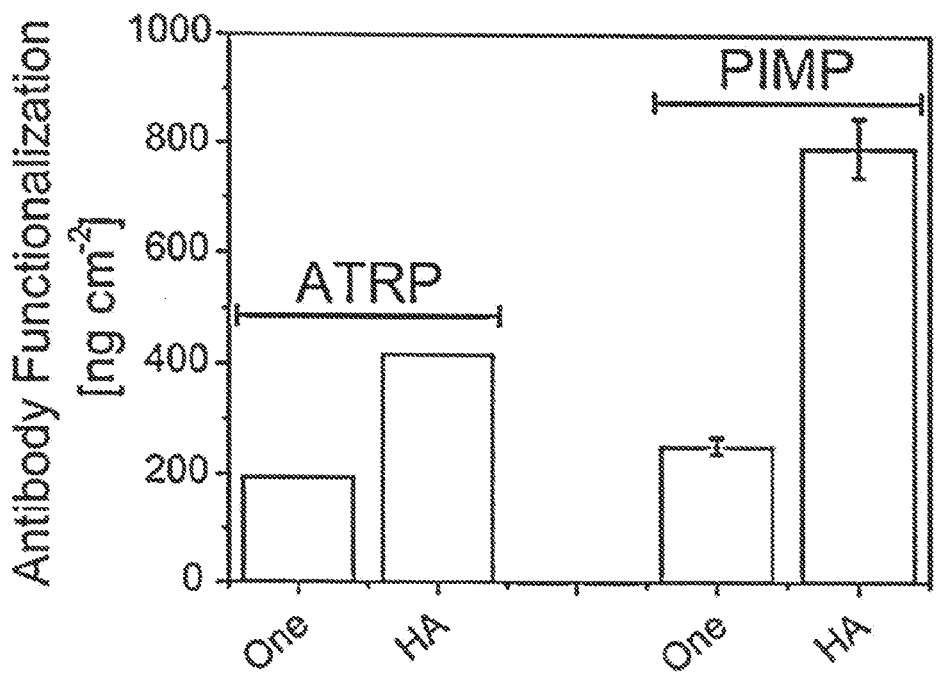
FIGS. 10A-C: 10A: IgG functionalization levels on films with one-layer (One) and hierarchical (HA) structures prepared via SI-ATRP and SI-PIMP. 10B: Fouling levels in the presence of undiluted serum or plasma, before and after IgG functionalization. 10C: Antigen detection from PBS.

In this study, functionalization and fouling tests were monitored in situ using a custom-built SPR sensor with wavelength modulation. For antibody immobilization, the films were activated using EDC/NHS coupling chemistry followed by injecting an anti-human thyroid stimulating hormone (anti-TSH) IgG solution. The unreacted NHS esters were then hydrolyzed back into the original carboxylate groups using 10 mM sodium carbonate buffer with 300 mM NaCl at pH 10. As shown in FIG. 10A, the functionalization levels were estimated as 195.9 ng $cm^{-2}$ and 417.0 ng $cm^{-2}$ for one-layer ("One" in FIGS. 10A-10C) and hierarchical ("HA" in FIGS. 10A-10C) films prepared via SI-ATRP; 253.0±14.8 and 792.7±54.7 ng $cm^{-2}$ for one-layer and hierarchical films from SI-PIMP. Here, an increase in binding capacities for IgG molecules on pCB films was observed for the hierarchical architecture. For the IgG functionalized one-layer films, the binding capacities were similar to that obtained with carboxyl-terminated SAMs. Although pCB provides abundant carboxyl groups for biomolecule conjugation, highly-packed polymer brushes hamper the penetration of molecules due to steric hindrance and therefore modification only takes place at the accessible functional groups on the topmost layer of the pCB films. However, for the hierarchical films, the chain densities of the second layer were controlled via the termination and regeneration approaches. Constructed from highly dense first layers, the loose second layers allowed diffusion of antibodies thus enabling conjugation with NHS esters throughout the entire second layer. The control experiments using the structured films without treatment of capped species were also conducted. IgG immobilization levels were reduced by 30% and 64% for SI-ATRP and SI-PIMP, respectively, compared to the corresponding treated hierarchical pCB films. This evidence indicates that a sufficient number of accessible binding groups for protein modification, made apparent by the larger second-layer film thicknesses of the treated films, are a determining factor of the ligand loading capacity.

Figure 11:
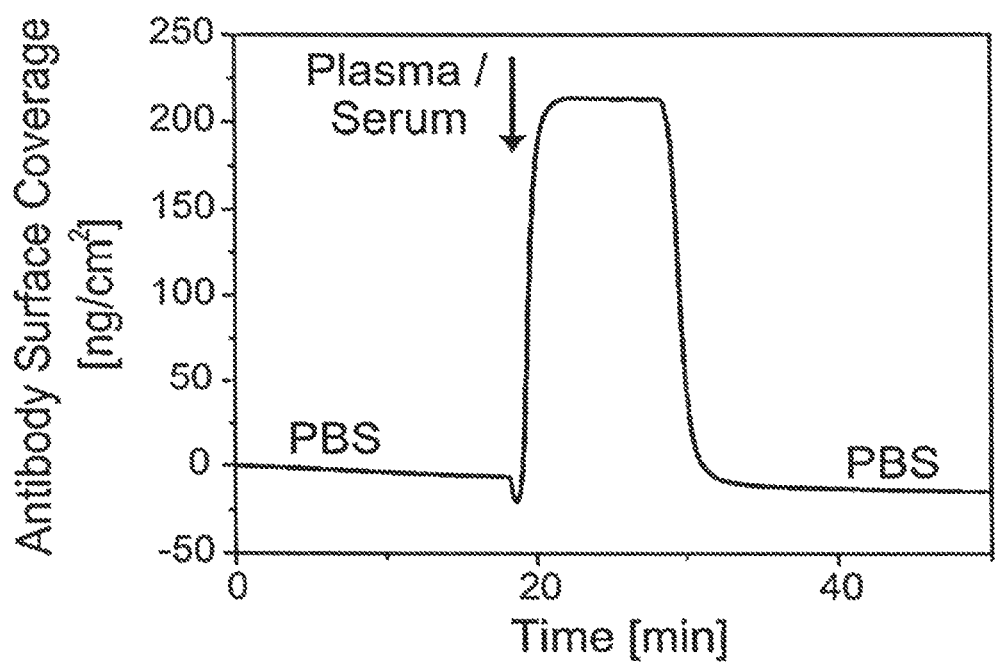
FIG. 11: The SPR sensorgram for the fouling test in the presence of undiluted blood plasma or serum on hierarchical pCB films.
Figure 12:
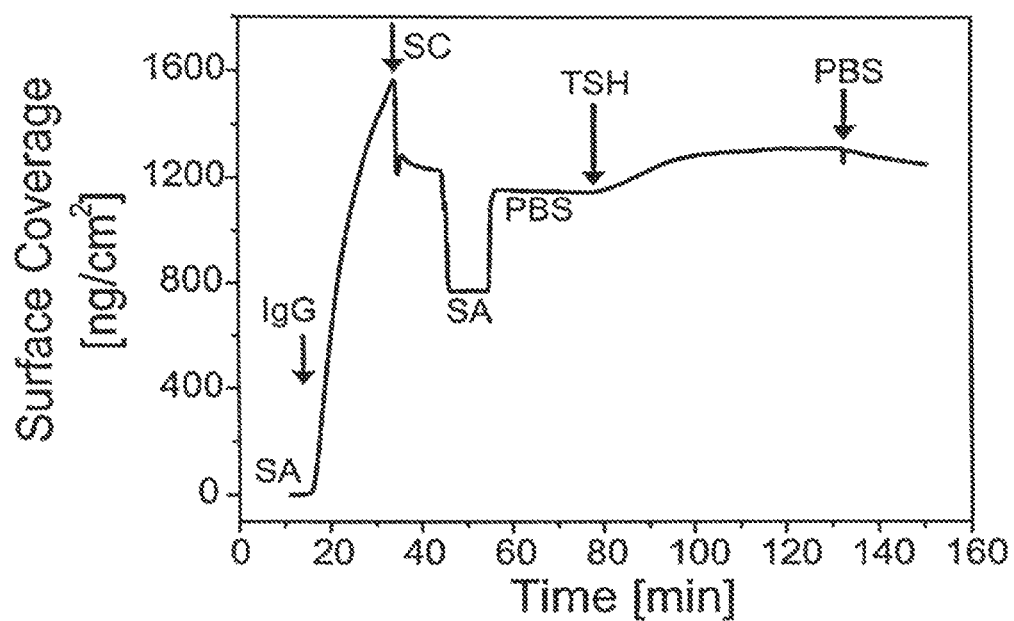
FIG. 12: Following EDC/NHS activation, the pCB films were modified with TSH IgG, deactivated with SC buffer, and then used for TSH antigen detection.

FIG. 11 is an SPR sensorgram for the fouling test in the presence of undiluted blood plasma or serum on hierarchical pCB films. FIG. 12 is an SPR sensorgram following EDC/NHS activation, the pCB films were modified with TSH IgG, deactivated with SC buffer, and then used for TSH antigen detection.

Figure 10B:
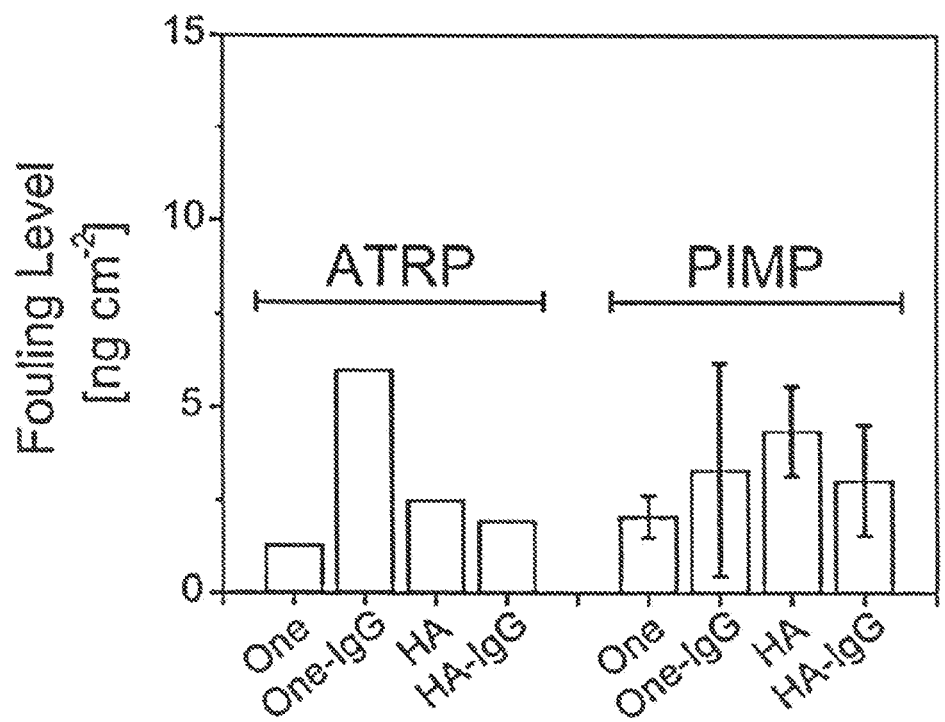
Figure 10C:
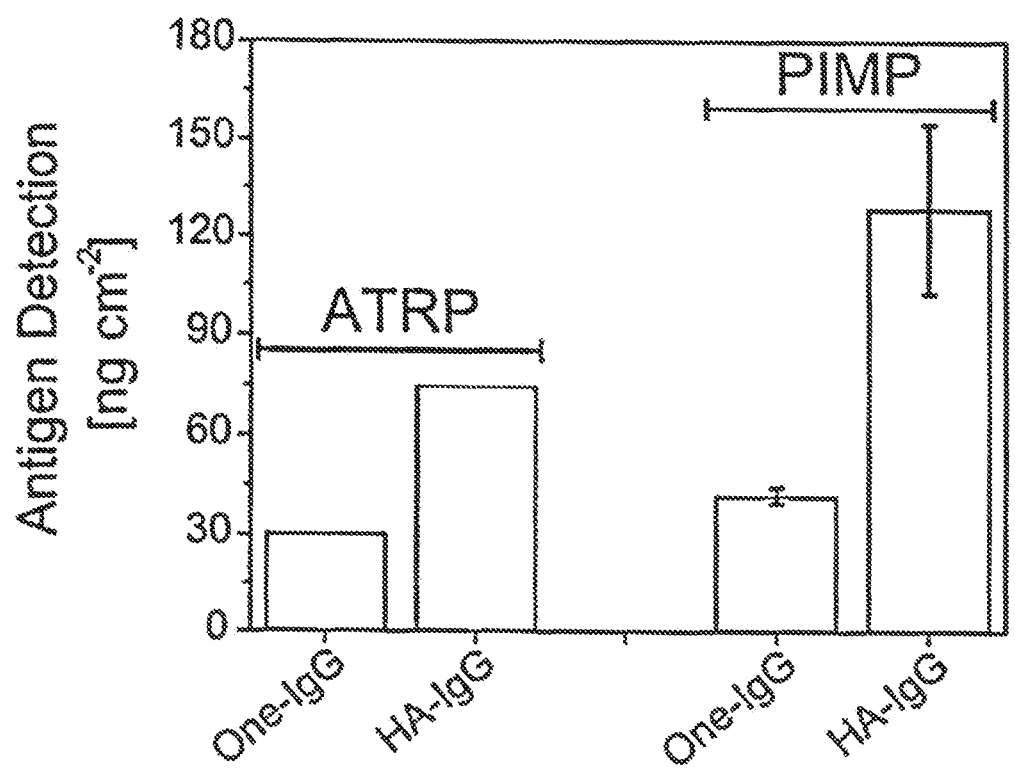

The protein fouling levels on one-layer films and hierarchical pCB films before and after IgG functionalization were tested by flowing undiluted blood serum or plasma (FIG. 10B). All fouling levels were very low as a result of the highly-packed first pCB layers serving as ultra low fouling backgrounds. As a comparison, the fouling level for a loose pCB one-layer film with a thickness of 12.3 nm prepared from 50% water in methanol by SI-PIMP was as high as 54.3 ng cm$^{-2}$ in the presence of serum. These results indicate that the high performance of pCB for effective resistance against non-specific adsorption and high ligand loading is established on the basis of control over the polymer architecture.

Solutions containing TSH antigen were flowed over the functionalized surfaces to evaluate the antigen detection ability (FIG. 10C) and the bio-activities (molar ratios of antigen to antibody) of the binding platforms. TSH binding capacities were 42.1±2.4 ng cm$^{-2}$ and 128.5±26.2 ng cm$^{-2}$ for one-layer and hierarchical pCB films from SI-PIMP, respectively. The corresponding bio-activities were 0.89 and 0.87. The one-layer and hierarchical pCB films made via SI-ATRP bound 30.4 ng cm$^{-2}$ and 74.7 ng cm$^{-2}$ of TSH, respectively, with bio-activities of 0.80 and 0.93. Thus, this study demonstrates that the binding capacity for antigens is well correlated to the degree of antibody immobilization and that the bio-activity of the film is not affected by the pCB hierarchical architecture.

In conclusion, new methodologies were developed for creating surface-initiated polymer brushes with hierarchical architectures possessing distinctive structurally regulated functionalities. Through combining the benefits of 2D and 3D polymer structures, a unique binding platform with ultra low fouling and high loading was established to serve as a new model for advancing surface chemistry needs. While this work was demonstrated with pCB prepared via the "grafting from" approach using a SPR biosensor, this is a powerful and yet generic concept which can be applied to other surface chemistries, such as dextran or PEG-based materials, and is easily adaptable to other sensing platforms and devices. Furthermore, the preparation method for the hierarchical architecture can be modified for other applications, such as "click" or thiol-ene "grafting to" chemistries. This research illustrates the great promise of this hierarchical surface coating development for multi-functional surface chemistry in biotechnological and nano-engineering applications.

Experimental Methods pCB Films Via SI-ATRP

Mercaptoundecyl bromoisobutyrate (SI-ATRP initiator) and carboxybetaine acrylamide (CB) monomer were synthesized as described previously. SAMs on cleaned SPR chips of ATRP initiator were formed by soaking overnight in ethanol (0.1 mM). Upon removal, the chips were rinsed with ethanol, THF, ethanol, and then dried and placed in a custom glass tube reactor under nitrogen. In a separate glass tube, CuBr (8.86 mg), 2,2'-bipyridine (57.85 mg), and CB (600 mg) were added and placed under nitrogen. The solids were dissolved in nitrogen purged methanol (4 mL) and transferred to the chips and reacted for 24 hours at 25° C. in a shaker bath. For single layer films, the chips were rinsed with water and stored overnight in PBS. For hierarchical films, the solution was quenched with CuBr$_2$ (275.87 mg) in methanol (4 mL) and then rinsed with methanol, water, and submerged in PBS. The second block was then grown via repeating the above procedure but using a nitrogen purged methanol:water (1:1) and reacting for 3 hours. Termination of bromine groups and replacement with non-reactive azide moieties for reducing the second block polymer density was achieved by submerging the single layer chips in an aqueous azide solution (0.1 M) for 2 hours, removing and rinsing with PBS, water, and then drying for ATRP.

pCB Films Via SI-PIMP

The DTCA photoiniferter was synthesized as described previously. SAMs on cleaned SPR chips of the photoiniferter were formed by soaking overnight in THF containing DTCA (2 mM) followed by rinsing with THF and drying with a stream of air. For single layers, the photoiniferter modified chip was transferred to a quartz reaction tube along with 170 mg of CB monomer and placed under nitrogen. Nitrogen purged methanol (5 mL) containing TED (2 μM) was transferred to the reaction tube. The photo-polymerization was then conducted for 30 min using a UV lamp (302 nm) coupled with a 280 nm cutoff filter for preventing deterioration of thiol-gold bonds. Following the reaction, the chips were removed and rinsed with water, PBS, and then submerged in PBS. For the hierarchical films, the single layer film was re-initiated using the identical procedure except for the using nitrogen purged methanol:water (10:90) in the absence of TED.

Ellipsometry

The thickness of the pCB films were determined using an ellipsometer (Model alpha-SE, J. A. Woollam, Lincoln, Nebr.) using the 380-900 nm wavelength range at an incidence angle of 70°. The results were fitted to a Cauchy module.

Non-Specific Protein Adsorption, Antibody Modification, and Antigen Detection

The non-specific adsorption, antibody immobilization, and antigen detection was monitored using a custom-built four-channel SPR sensor with the Kretschmann configuration and wavelength modulation as described previously.

SPR chips were made of a glass slide coated with titanium (2 nm) followed by gold (48 nm) using an electron beam evaporator. A 1 nm SPR wavelength shift corresponded to a change in the protein surface coverage of 17 ng cm$^{-2}$ which was corrected to account for loss of sensitivity due to the polymer films using previously described methods. For fouling experiments, undiluted human serum or plasma were injected (10 min, 40 µL min$^{-1}$) and the wavelength shift between PBS baselines was converted to a surface coverage. Anti-TSH was immobilized by first injecting 10 mM sodium acetate (SA, pH 5) followed by EDC/NHS (0.2 M/0.05 M in water) for 7 min at 30 µL min$^{-1}$. Anti-TSH (50 µg mL$^{-1}$ in 10 mM HEPES pH 7.5) was injected (20 min, 20 µL min$^{-1}$) followed by deactivating with 10 mM sodium carbonate containing 300 mM sodium chloride (pH 10) for 10 min and the SA both at 30 µL min$^{-1}$. Immobilization was calculated as the difference between SA baselines before IgG injection and after deactivation. TSH was antigen binding was then monitored by first injecting PBS and then antigen (1 µg mL$^{-1}$ in PBS at 40 µL min$^{-1}$) following by PBS.

Materials

Copper (I) Bromide (99.999%), 2,2'-bipyridine (BPY, 99%), tetrahydrofuran (THF), Tetraethylthiuram disulfide (TED), methanol, 4-(2-hydroxyethyl)-1-piperazineethane-sulfonic acid (HEPES), and phosphate buffered saline (PBS, 0.01 M phosphate, 0.138 M sodium chloride, 0.0027 M potassium chloride, pH 7.4) were purchased from Sigma-Aldrich (St. Louis, Mo.). Ethanol (200 Proof) was purchased from Decon Laboratories (King of Prussia, Pa.). Sodium carbonate anhydrous was purchased from EMD Chemicals (Darmstadt, Germany). Sodium chloride (NaCl) and ether were purchased from J. T. Baker (Phillipsburg, N.J.). Sodium acetate anhydrous was purchased from Fluka (subsidiary of Sigma Aldrich, St. Louis, Mo.). 1-Ethyl-3-(3-dimethylaminopropyl)carbodiimide hydrochloride (EDC) and N-hydroxysuccinimide (NHS) were purchased from Acros Organics (Geel, Belgium). Pooled human serum was purchased from Biochemed Services (Winchester, Va.). Antibody to thyroid stimulating hormone (anti-TSH) and the TSH antigen were purchased from ThermoFisher Scientific (Waltham, Mass.). Water used in the experiments was purified using a Millipore water purification system with a minimum resistivity of 18.2 MΩ cm.

Exemplary Embodiment 3

Blood Typing

Direct Typing

Figure 13:
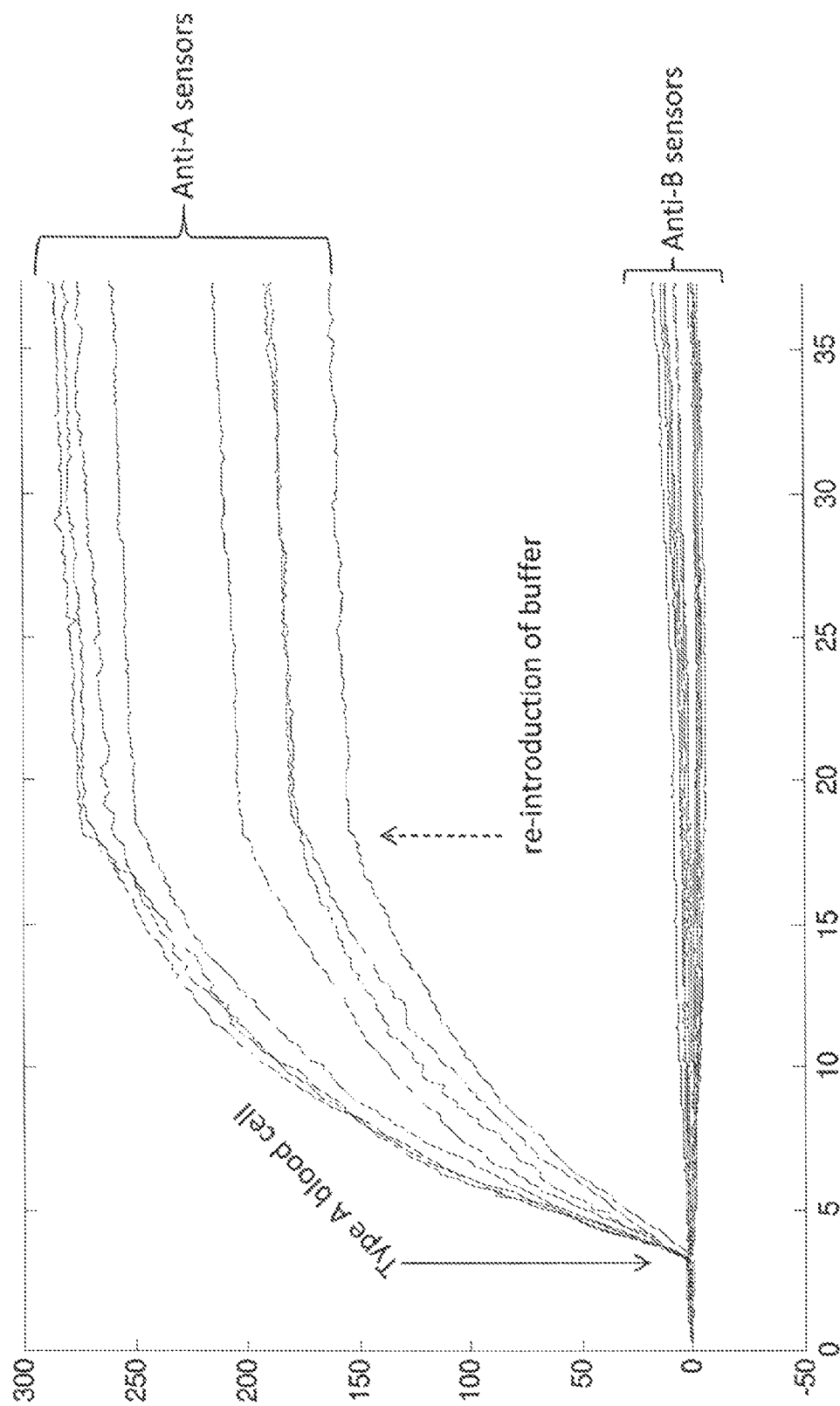
FIG. 13: Test data for type A red blood cells detected in solution using ring resonator photonic devices in accordance with the embodiments disclosed herein.
Figure 14:
FIG. 14: Test data for type B red blood cells detected in solution using ring resonator photonic devices in accordance with the embodiments disclosed herein.

To prepare biosensor chips for direct red blood cell (RBC) typing assays, microring resonator arrays were coated with adsorbed Protein A. After briefly washing the chip, monoclonal anti-blood group IgG antibodies (anti-A and anti-B) as well as a negative control monoclonal IgG (antiPSA) were microspotted on separate regions of each chip. The entire biosensor chip was blocked with bovine serum albumin to minimize non-specific adsorption of red blood cell fragments. The membranes of red blood cells (Type A or Type B RBCs) were ruptured by resuspending cells in a hypotonic lysis buffer, and cell fragments were washed via centrifugation to remove expelled cellular contents including hemoglobin from solution. Ruptured red blood cells were diluted in phosphate-buffered saline and introduced to functionalized sensor arrays at a flow rate of 20 µl/min for 15 minutes. The sensor responses of anti-A and anti-B functionalized microring resonators were normalized to the response of the negative control antiPSA sensors. The results of a plurality of anti-A and anti-B sensors are presented in FIG. 13 (testing for Type A RBC) and FIG. 14 (testing for Type B RBC). The specific detection of both Type A and Type B RBC is apparent from the disclosed data.

Indirect Typing

Figure 15:
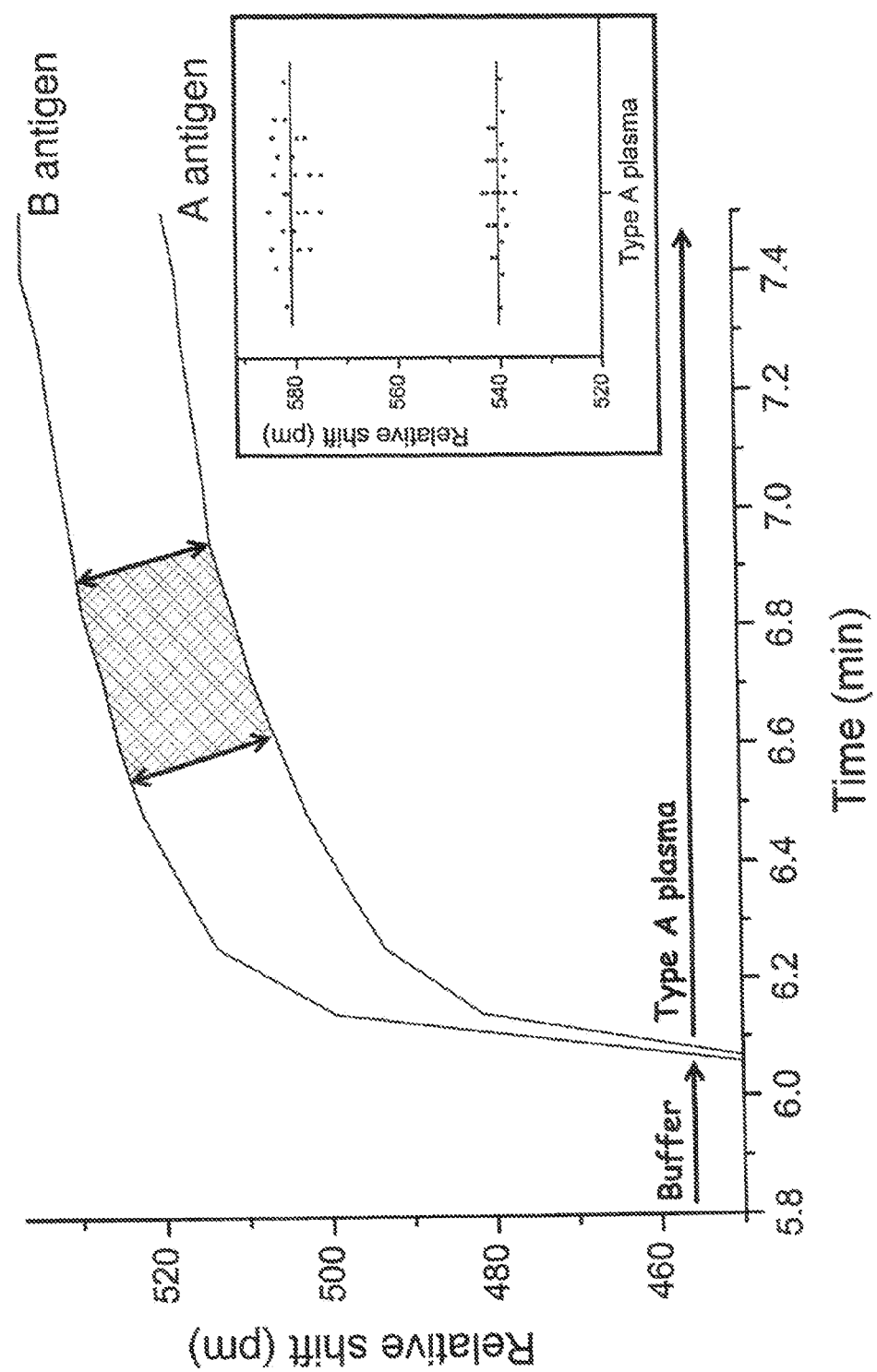
FIG. 15: Test data for type A and B antigen detected in type A plasma using ring resonator photonic devices in accordance with the embodiments disclosed herein.
Figure 16:
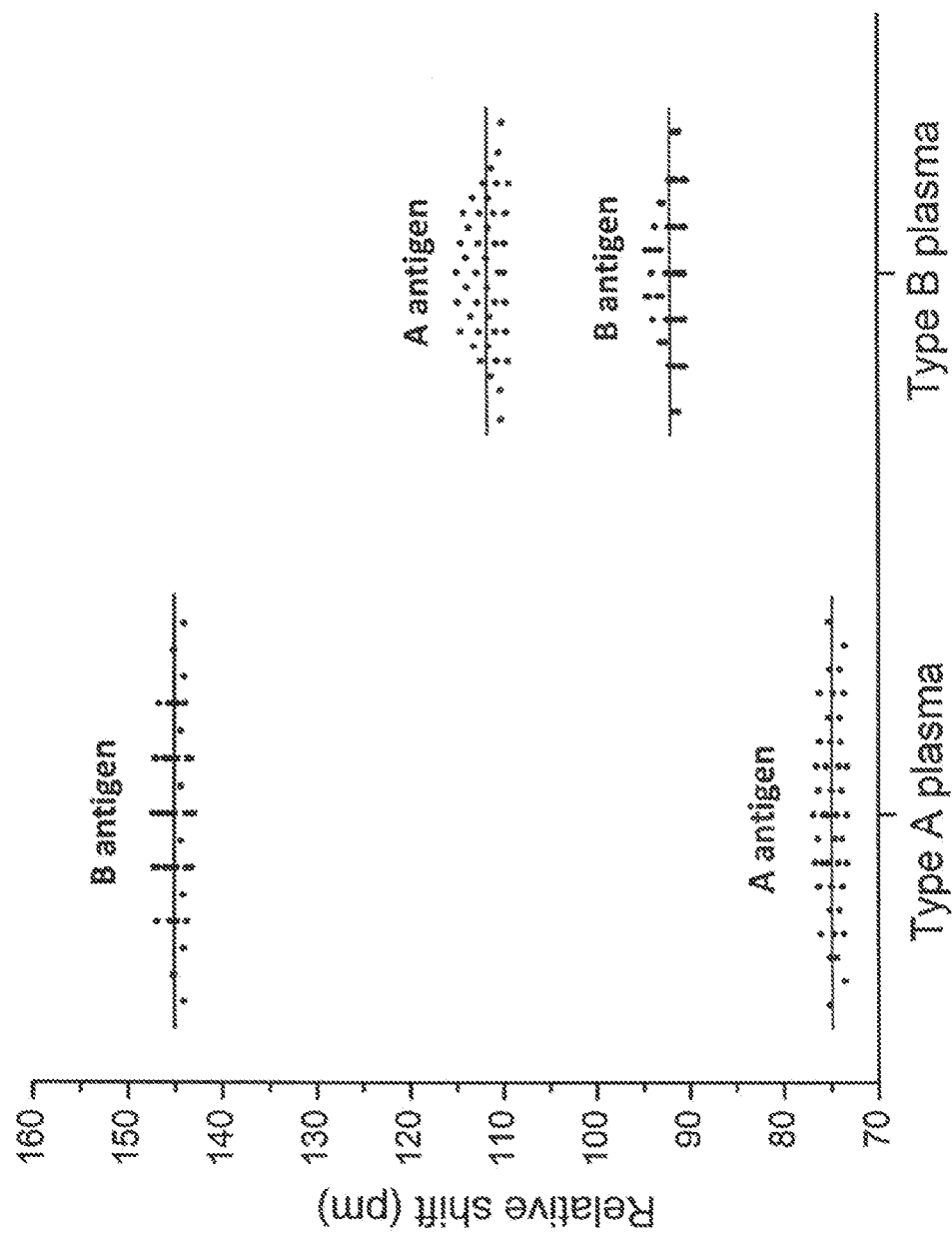
FIG. 16: Test data summary for detecting type A and B antigens in type A and B plasma using ring resonator photonic devices in accordance with the embodiments disclosed herein.

Arrays of microring resonators were coated with the non-fouling DpC zwitterionic polymer as previously described herein. Surface grafted-DpC polymer chains were chemically modified to covalently immobilize the streptavidin (SA) protein for further derivatization of the sensors with biotinylated capture elements. SA-DpC microrings were microspotted with biotinylated blood group antigens (A and B antigens) for specific capture of anti-blood group antibodies from human sera. Functionalized sensor arrays were then exposed to undiluted human plasma (Type A or Type B plasma), and the differential sensor response was compared to determine the presence of anti-blood group antibodies in blood samples. The testing of sensors exposed to type A plasma is illustrated in FIG. 15. A summary of test data from multiple sensors exposed to both type A and type B plasma is illustrated in FIG. 16. The consistency of the results presented in FIGS. 15 and 16 demonstrate the usefulness of the photonic devices to determine blood type.

While illustrative embodiments have been illustrated and described, it will be appreciated that various changes can be made therein without departing from the spirit and scope of the invention.

The embodiments of the invention in which an exclusive property or privilege is claimed are defined as follows:

1. A photonic system for testing a sample to determine a blood type, comprising:
   (1) a first photonic device for determining the blood type, comprising:
   a first sample waveguide having a first sample surface; and
   a first binding coating covering and in optical communication with at least a portion of the first sample surface, the first binding coating being configured to directly bind to a blood cell target moiety in the sample indicative of the blood type, wherein the blood cell target moiety is attached to a blood cell body selected from the group consisting of a blood cell, a blood cell membrane, a blood cell fragment, a microvesicle, a microparticle, and a blood cell-associated antigen, and wherein the first photonic device is configured such that light passed through the first sample waveguide has an evanescent field that extends a distance beyond the first sample waveguide sufficient to detect the bound blood cell target moiety; and
   (2) a second photonic device for determining blood type, comprising:
   a second sample waveguide having a second sample surface; and
   a second binding coating covering and being in optical communication with at least a portion of the second sample surface, the second binding coating comprising specifically defined antigens configured to bind to an antibody in the sample indicative of immunity to blood antigens, wherein the second photonic device is configured such that light passed through the second sample waveguide has an evanescent field that extends a distance beyond the second sample waveguide sufficient to detect the antibody indicative of immunity to blood antigens, wherein the first photonic device and the second photonic device are configured to simultaneously test the sample.

2. The photonic system of claim 1, wherein the first photonic device and the second photonic device are configured to simultaneously determine the blood type.

3. The photonic system of claim 1, further comprising a computer configured to determine the blood type using output from both the first photonic device and the second photonic device.

4. The photonic system of claim 1, further comprising a reference waveguide in optical communication with the sample that does not have any binding coating.

5. The photonic system of claim 1, further comprising a third photonic device configured to bind a target moiety in the sample indicative of a pathogen.

6. The photonic system of claim 5, wherein the target moiety indicative of a pathogen is selected from the group consisting of a pathogen, a pathogen-associated antibody, a pathogen-associated nucleic acid, and a pathogen-associated antigen.

7. The photonic system of claim 1, wherein the sample is whole blood.

8. The photonic system of claim 1, wherein the first sample waveguide and the second sample waveguide are each a portion of a photonic device selected from the group consisting of a ring resonator, a Bragg reflector, and a Mach-Zehnder interferometer.

9. The photonic system of claim 8, wherein the first sample waveguide and the second sample waveguide are each a portion of the same type of photonic device.

10. The photonic system of claim 1, wherein the first binding coating is antifouling, the second binding coating is antifouling, or the first binding coating and the second binding coating are antifouling.

11. The photonic system of claim 1, wherein the first binding coating is zwitterionic, the second binding coating is zwitterionic, or the first binding coating and the second binding coating are zwitterionic.

12. The photonic system of claim 1, wherein the first binding coating comprises a plurality of layers, including an antifouling layer and a capture layer.

13. The photonic system of claim 12, wherein the capture layer comprises at least one binding moiety configured to directly bind to the blood cell target moiety indicative of blood type.

14. The photonic system of claim 12, wherein the antifouling layer is bound to the capture layer.

15. The photonic system of claim 1, wherein the first binding coating is covalently attached to the first sample waveguide.

16. The photonic system of claim 1, wherein the first binding coating is not bound to the first sample waveguide.

17. The photonic system of claim 1, wherein the second binding coating comprises a plurality of layers, including an antifouling layer and a capture layer.

18. The photonic system of claim 17, wherein the capture layer comprises the specifically defined antigens configured to bind to an antibody indicative of immunity to blood antigens.

19. The photonic system of claim 17, wherein the antifouling layer is bound to the capture layer.

20. The photonic system of claim 1, wherein the second binding coating is covalently attached to the second sample waveguide.

21. The photonic system of claim 1, wherein the second binding coating is not bound to the second sample waveguide.

22. The photonic system of claim 6, wherein the third photonic device comprises a third binding coating, wherein the third binding coating comprises a plurality of layers, including an antifouling layer and a capture layer, wherein the capture layer comprises specifically defined antigens configured to bind to the target moiety in the sample indicative of a pathogen.

* * * * *